United States Patent
Okabe et al.

(10) Patent No.: US 11,382,584 B2
(45) Date of Patent: *Jul. 12, 2022

(54) DISPLAY CONTROL DEVICE, METHOD FOR OPERATING DISPLAY CONTROL DEVICE, AND PROGRAM FOR OPERATING DISPLAY CONTROL DEVICE

(71) Applicant: FUJIFILM Corporation, Tokyo (JP)

(72) Inventors: Yuki Okabe, Tokyo (JP); Eiichi Imamichi, Tokyo (JP); Yuya Kudo, Tokyo (JP); Masaki Miyamoto, Tokyo (JP)

(73) Assignee: FUJIFILM Corporation, Tokyo (JP)

( * ) Notice: Subject to any disclaimer, the term of this patent is extended or adjusted under 35 U.S.C. 154(b) by 55 days.

This patent is subject to a terminal disclaimer.

(21) Appl. No.: 16/845,027

(22) Filed: Apr. 9, 2020

(65) Prior Publication Data

US 2020/0323504 A1 Oct. 15, 2020

(30) Foreign Application Priority Data

Apr. 11, 2019 (JP) .............................. JP2019-075795

(51) Int. Cl.
*A61B 6/00* (2006.01)
*G06F 3/0482* (2013.01)
(Continued)

(52) U.S. Cl.
CPC .............. *A61B 6/463* (2013.01); *A61B 5/743* (2013.01); *A61B 5/7425* (2013.01);
(Continued)

(58) Field of Classification Search
CPC .................... G06T 7/38; G06T 7/0014; G06T 2207/10072; G06F 3/0482; G06F 3/1415;
(Continued)

(56) References Cited

U.S. PATENT DOCUMENTS 9,626,477 B2 * 4/2017 Wang .................... G16H 30/40
2007/0242069 A1 10/2007 Matsue et al.
(Continued)

FOREIGN PATENT DOCUMENTS

JP 2010086149 4/2010
JP 4820680 11/2011
(Continued)

OTHER PUBLICATIONS

"Office Action of Japan Counterpart Application" with English translation thereof, dated May 31, 2022, p. 1-p. 5.

*Primary Examiner* — Andrew L Tank
(74) *Attorney, Agent, or Firm* — JCIPRNET

(57) ABSTRACT

A display control device includes: a first display control unit that display, on a display screen, a display region in which a plurality of display frames are arranged and a selection region in which a list of a plurality of thumbnail images is displayed; a first receiving unit that receives an operation of selecting the plurality of thumbnail images to select the plurality of examination images; a second receiving unit that receives an operation of designating an arrangement direction of the plurality of selected examination images in the display region in a state in which the plurality of thumbnail images are selected and before the plurality of examination images are laid out in the plurality of display frames; and a second display control unit that lays out the plurality of examination images in the plurality of display frames in the designated arrangement direction and displays the plurality of examination images on the display screen.

22 Claims, 24 Drawing Sheets

(51) Int. Cl.
  *G06F 3/14*    (2006.01)
  *A61B 5/00*    (2006.01)
  *G06T 7/00*    (2017.01)
  *G06T 7/38*    (2017.01)

(52) U.S. Cl.
  CPC .......... *A61B 5/7435* (2013.01); *A61B 5/7475* (2013.01); *A61B 6/465* (2013.01); *G06F 3/0482* (2013.01); *G06F 3/1415* (2013.01); *G06T 7/0014* (2013.01); *G06T 7/38* (2017.01); *G06T 2207/10072* (2013.01)

(58) Field of Classification Search
  CPC ....... A61B 6/463; A61B 5/743; A61B 5/7425; A61B 5/7435; A61B 5/7475; A61B 6/465; G16H 10/60
  See application file for complete search history.

(56) References Cited

U.S. PATENT DOCUMENTS

| | | | | |
|---|---|---|---|---|
| 2009/0132588 | A1* | 5/2009 | Mahesh | G16H 40/63 |
| 2010/0083154 | A1 | 4/2010 | Takeshita | |
| 2013/0088512 | A1* | 4/2013 | Suzuki | G16H 10/60 |
| | | | | 345/629 |
| 2014/0310648 | A1* | 10/2014 | Braun | G16Z 99/00 |
| | | | | 715/800 |

FOREIGN PATENT DOCUMENTS

| | | |
|---|---|---|
| JP | 2015208602 | 11/2015 |
| JP | 2019032908 | 2/2019 |

\* cited by examiner

DISPLAY CONTROL DEVICE, METHOD FOR OPERATING DISPLAY CONTROL DEVICE, AND PROGRAM FOR OPERATING DISPLAY CONTROL DEVICE

CROSS-REFERENCE TO RELATED APPLICATION

This application claims priority from Japanese Patent Application No. 2019-075795, filed on Apr. 11, 2019, the disclosure of which is incorporated by reference herein in its entirety.

BACKGROUND

Field of the Invention

The present disclosure relates to a display control device, a method for operating a display control device, and a program for operating a display control device.

Related Art

In recent years, in the field of medical image diagnosis, in addition to X-ray imaging apparatuses, imaging apparatuses (hereinafter, referred to as modalities) using various techniques, such as computed tomography (CT) apparatuses, ultrasound (US) diagnostic apparatuses, magnetic resonance imaging (MRI) apparatuses, positron emission tomography (PET) apparatuses, and single-photon emission computed tomography (SPECT) apparatuses, have been used. In the modalities, a plurality of examination images are acquired in one examination. Then, a plurality of series, each of which includes a plurality of examination images acquired for each examination, are acquired by different modalities under different imaging conditions.

In contrast, in the related art, comparative interpretation has been performed which displays a plurality of examination images on a display device, such as a liquid crystal display, and interprets the examination images while comparing the examination images. For example, for the examination image of a patient that is an example of a subject, the examination images of the same patient in the current examination and the past examination are displayed and comparative interpretation is performed to check the degree of progress of a lesion or to find abnormality at an early stage. In addition, in many cases, comparative interpretation is performed for a plurality of examination images acquired in a plurality of different types of examinations, such as a CT examination and an ultrasound examination, to obtain useful diagnosis results.

Therefore, various techniques have been proposed in order to facilitate an operation of designating the layout position of examination images in a case in which a plurality of examination images to be subjected to comparative interpretation are displayed in a display region for observation on a display screen.

In the display control devices described in JP2019-032908A and JP4820680B, a thumbnail image obtained by reducing the examination image is displayed on the display screen in addition to the display region for observation. Then, one thumbnail image is selected and the operation of designating the layout position of the examination image in the display region for observation is received according to the position where the selected thumbnail image is dropped.

However, in the techniques described in JP2019-032908A and JP4820680B, the thumbnail images are selected one by one and the layout position of one examination image corresponding to the selected thumbnail image is designated by a drag and drop operation for the selected thumbnail image. Therefore, in a case in which a plurality of examination images are laid out, the operation needs to be repeated by the number of examination images to be laid out. As a result, as the number of examination images becomes larger, the operation becomes more complicated.

In a case in which a plurality of examination images are displayed in the display region, the arrangement direction of the plurality of examination images may change depending on, for example, the purpose of observation and user preference. It is desirable to designate the arrangement direction with a simple operation in order to flexibly respond to the change.

SUMMARY

The present disclosure has been made in view of the above-mentioned problems and an object of the present disclosure is to provide a display control device, a method for operating a display control device, and a program for operating a display control device which can lay out a plurality of examination images in a desired arrangement direction with a simple operation, as compared to a case in which the layout position of each examination image is designated in the layout of the examination images in a display region.

According to the present disclosure, there is provided a display control device comprising: a first display control unit that performs first display control to display, on a display screen, a display region in which a plurality of examination images acquired for each examination are displayed and which has a plurality of display frames capable of being laid out as display positions of the plurality of examination images and a selection region which is used to select the plurality of examination images laid out in the plurality of display frames and in which a list of a plurality of thumbnail images obtained by reducing each of the plurality of examination images is displayed; a first receiving unit that receives an operation of selecting the plurality of thumbnail images from the selection region to select the plurality of examination images corresponding to the plurality of thumbnail images; a second receiving unit that receives an operation of designating an arrangement direction of the plurality of selected examination images in the display region in a state in which the plurality of thumbnail images are selected in the selection region and before the plurality of examination images are laid out in the plurality of display frames; and a second display control unit that performs second display control to lay out the plurality of examination images in the plurality of display frames in the designated arrangement direction and to display the plurality of examination images laid out in the plurality of display frames on the display screen.

In the display control device according to the present disclosure, the second receiving unit may receive an operation of designating a vertical direction or a horizontal direction as the arrangement direction.

In the display control device according to the present disclosure, the designation operation received by the second receiving unit is not limited to the operation of designating the vertical direction and the horizontal direction, but may be an operation of designating an oblique direction.

In the display control device according to the present disclosure, a mode in which the second receiving unit receives the operation of designating the arrangement direction may include a window mode that uses any one of the display region in which the plurality of display frames are arranged or a miniature window which is displayed in the display screen separately from the display region and in which the arrangement of the plurality of display frames is reduced as a designation window for designating the arrangement direction and that receives the operation of designating the arrangement direction through the designation window.

In the display control device according to the present disclosure, the designation operation may be an operation of designating an inside or a frame line of one of the plurality of display frames in the designation window, and the second receiving unit may receive designation of the vertical direction or the horizontal direction as the arrangement direction according to a designated position in the inside or on the frame line.

In the display control device according to the present disclosure, the designated position may be a vertical side and a horizontal side among the frame lines of the display frame. In addition, the inside of the display frame may be divided into a plurality of small regions and any one of the divided small regions may be used as the designated position.

In the display control device according to the present disclosure, the second receiving unit may set the display frame including the designated position among the plurality of display frames as a first display frame of the plurality of examination images which are laid out.

In the display control device according to the present disclosure, the designation operation may be an operation of designating an outer peripheral portion of the designation window, and the second receiving unit may receive the designation of the vertical direction or the horizontal direction as the arrangement direction according to a designated position in the outer peripheral portion.

In the display control device according to the present disclosure, the outer peripheral portion may be, for example, on a frame line of the outer frame of the designation window or may be outside the frame line. In the case of a frame with a thick frame line, a designation button may be displayed in the frame line.

In the display control device according to the present disclosure, the operation of designating the arrangement direction through the designation window may be an operation of dragging the plurality of thumbnail images selected in the selection region from the selection region to the designated position and dropping the thumbnail images at the designated position.

In the display control device according to the present disclosure, the designation operation is not limited to the drag and drop operation and may be an operation of selecting a thumbnail image and then clicking a designated position with, for example, a pointer indicating a position.

In the display control device according to the present disclosure, the window mode may use the miniature window in which a plurality of miniature display frames are arranged as the plurality of display frames.

In the display control device according to the present disclosure, on the display screen, the miniature window may not be displayed before the plurality of thumbnail images are selected and may be displayed in a case in which the drag is started after the plurality of thumbnail images are selected.

In the present disclosure, "the case in which the drag is started" may be the timing when the drag operation is started or immediately before the drag operation is started, specifically, the timing when a left button of a mouse is pressed on a region of any one of the plurality of thumbnail images.

Further, in the display control device according to the present disclosure, the miniature window may be displayed at a position where a drag distance of the thumbnail image from the selection region to the designated position is shorter than that in a case in which the display region is used as the designation window.

In the display control device according to the present disclosure, in a case in which the examination image has been laid out in at least one of the display frames in the display region, and related information related to the laid-out examination image may be displayed in the miniature display frame corresponding to the display frame of the display region in which the examination image has been laid out among the plurality of miniature display frames in the miniature window.

In the display control device according to the present disclosure, the related information may be text information.

In the display control device according to the present disclosure, the text information preferably includes at least one of a character, a number, or a symbol.

In the display control device according to the present disclosure, the mode in which the second receiving unit receives the operation of designating the arrangement direction may include a menu mode that displays a menu in which the vertical direction and the horizontal direction capable of being designated as the arrangement direction are displayed on the display screen and receives the operation of designating the arrangement direction through the menu.

In the display control device according to the present disclosure, any one of the window mode or the menu mode may be selected as the mode in which the second receiving unit receives the operation of designating the arrangement direction.

In the display control device according to the present disclosure, the first receiving unit may further receive a selection order in which the plurality of thumbnail images are selected, and the second display control unit may lay out the plurality of examination images in the plurality of display frames in the selection order.

In the display control device according to the present disclosure, the examination images displayed in the display frames in the display region may include a representative image of a plurality of examination images acquired in the same examination. In a case in which the examination image displayed in the display frame is the representative image, the plurality of examination images may be selectively displayed in the display frames.

According to the present disclosure, there is provided a method for operating a display control device. The method comprises: a first display control step of performing first display control to display, on a display screen, a display region in which a plurality of examination images acquired for each examination are displayed and which has a plurality of display frames capable of being laid out as display positions of the plurality of examination images and a selection region which is used to select the plurality of examination images laid out in the plurality of display frames and in which a list of a plurality of thumbnail images obtained by reducing each of the plurality of examination images is displayed; a first receiving step of receiving an operation of selecting the plurality of thumbnail images from the selection region to select the plurality of examination images corresponding to the plurality of thumbnail images; a second receiving step of receiving an operation of designating an arrangement direction of the plurality of selected examination images in the display region in a state in which the plurality of examination images are selected and before the plurality of examination images are laid out in the plurality of display frames; and a second display control step of performing second display control to lay out the plurality of examination images in the plurality of display frames in the designated arrangement direction and to display the plurality of examination images laid out in the plurality of display frames on the display screen.

According to the present disclosure, there is provided a program for operating a display control device. The program causes a computer to function as: a first display control unit that performs first display control to display, on a display screen, a display region in which a plurality of examination images acquired for each examination are displayed and which has a plurality of display frames capable of being laid out as display positions of the plurality of examination images and a selection region which is used to select the plurality of examination images laid out in the plurality of display frames and in which a list of a plurality of thumbnail images obtained by reducing each of the plurality of examination images is displayed; a first receiving unit that receives an operation of selecting the plurality of thumbnail images from the selection region to select the plurality of examination images corresponding to the plurality of thumbnail images; a second receiving unit that receives an operation of designating an arrangement direction of the plurality of selected examination images in the display region in a state in which the plurality of examination images are selected and before the plurality of examination images are laid out in the plurality of display frames; and a second display control unit that performs second display control to lay out the plurality of examination images in the plurality of display frames in the designated arrangement direction and to display the plurality of examination images laid out in the plurality of display frames on the display screen.

According to the present disclosure, there is provided another display control device comprising a memory that stores commands to be executed by a computer and a processor that is configured to execute the stored commands. The processor performs: a first display control step of performing first display control to display, on a display screen, a display region in which a plurality of examination images acquired for each examination are displayed and which has a plurality of display frames capable of being laid out as display positions of the plurality of examination images and a selection region which is used to select the plurality of examination images laid out in the plurality of display frames and in which a list of a plurality of thumbnail images obtained by reducing each of the plurality of examination images is displayed; a first receiving step of receiving an operation of selecting the plurality of thumbnail images from the selection region to select the plurality of examination images corresponding to the plurality of thumbnail images; a second receiving step of receiving an operation of designating an arrangement direction of the plurality of selected examination images in the display region in a state in which the plurality of examination images are selected and before the plurality of examination images are laid out in the plurality of display frames; and a second display control step of performing second display control to lay out the plurality of examination images in the plurality of display frames in the designated arrangement direction and to display the plurality of examination images laid out in the plurality of display frames on the display screen.

According to the display control device, the method for operating the display control device, and the program for operating the display control device of the present disclosure, it is possible to lay out a plurality of examination images in the user's preferred arrangement direction with a simple operation, as compared to a case in which the layout position of each examination image is designated.

DETAILED DESCRIPTION

Figure 1:
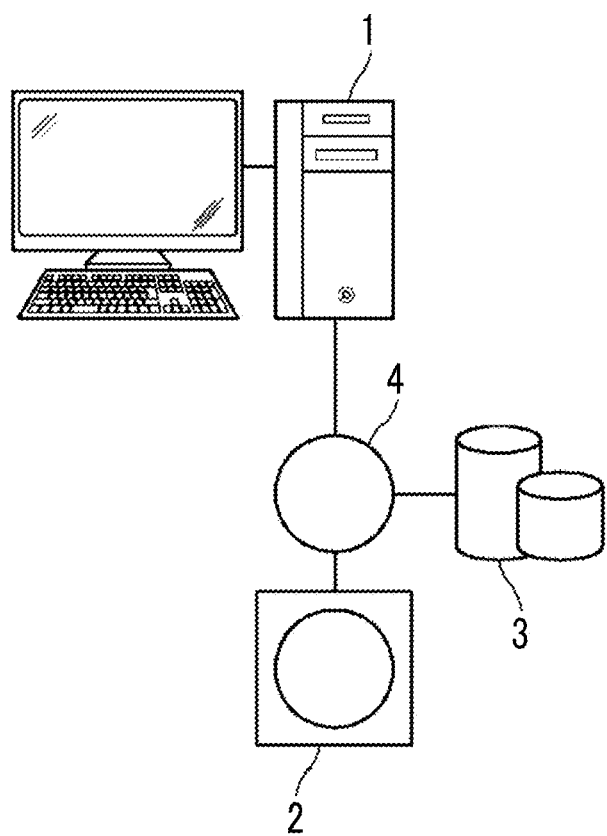
FIG. 1 is a hardware configuration diagram illustrating the outline of a diagnosis support system to which a display control device according to an embodiment of the present disclosure is applied.

Hereinafter, a first embodiment of the present disclosure will be described with reference to the drawings. FIG. 1 is a hardware configuration diagram illustrating the outline of a diagnosis support system to which a display control device according to an embodiment of the present disclosure is applied. As illustrated in FIG. 1, in the diagnosis support system, a display control device 1, a three-dimensional imaging apparatus 2, and an image storage server 3 according to this embodiment are connected to each other through a network 4 so as to be communicable.

The three-dimensional imaging apparatus 2 is an apparatus that captures an image of a diagnosis target part of a patient that is an example of a subject and generates a three-dimensional image indicating the part. Specifically, examples of the three-dimensional imaging apparatus 2 include a CT apparatus, an MRI apparatus, a PET apparatus, and a SPECT apparatus. An examination image generated by the three-dimensional imaging apparatus 2 is transmitted to the image storage server 3 and is then stored therein.

The image storage server 3 is a computer that stores and manages various kinds of data and comprises a large-capacity external storage device and database management software. The image storage server 3 communicates with other apparatuses through the wired or wireless network 4 to transmit and receive, for example, image data. Specifically, the image storage server 3 acquires various kinds of data including image data of the three-dimensional image generated by the three-dimensional imaging apparatus 2 through the network, stores the data in a recording medium, such as a large-capacity external storage device, and manages the stored data. The storage format of the image data and the communication between the apparatuses through the network 4 are based on a protocol such as Digital Imaging and Communication in Medicine (DICOM).

In this embodiment, the image storage server 3 stores various kinds of data including image data of a plurality of patients. For example, the image storage server 3 stores, as data stored for each patient, the three-dimensional image and accessory information of the patient acquired for each of the examinations performed for the same patient at different times and the three-dimensional image and accessory information of the patient acquired for each of the examinations performed for the same patient under different imaging conditions. For example, the image storage server 3 stores a plurality of series each of which includes a plurality of examination images acquired in one examination, such as abdominal CT or head MRI, for the current examination and the past examination. In the present disclosure, the three-dimensional image is a set of a plurality of slice images (tomographic images) output by a tomographic apparatus, such as a CT apparatus or an MRI apparatus, and is also referred to as volume data. Further, in the present disclosure, volume data acquired by one imaging operation is referred to as "series". In this embodiment, each of the plurality of slice images included in the series is an example of an examination image. Among the examination images, the examination images included in the same series are particularly referred to as same-series examination images.

The accessory information includes, for example, the following information: an image identification (ID) for identifying each image, a patient ID for identifying a subject, an examination ID for identifying an examination, a unique identification (UID) that is assigned to each examination image, an examination date and time when the examination image was generated, the type of modality used in the examination for acquiring the examination image, patient information including the name, age, and sex of a patient, an examination part (imaging part), imaging conditions (whether or not a contrast agent is used or a radiation dose), and a series number in a case in which a plurality of examination images are acquired by one examination.

Figure 2:
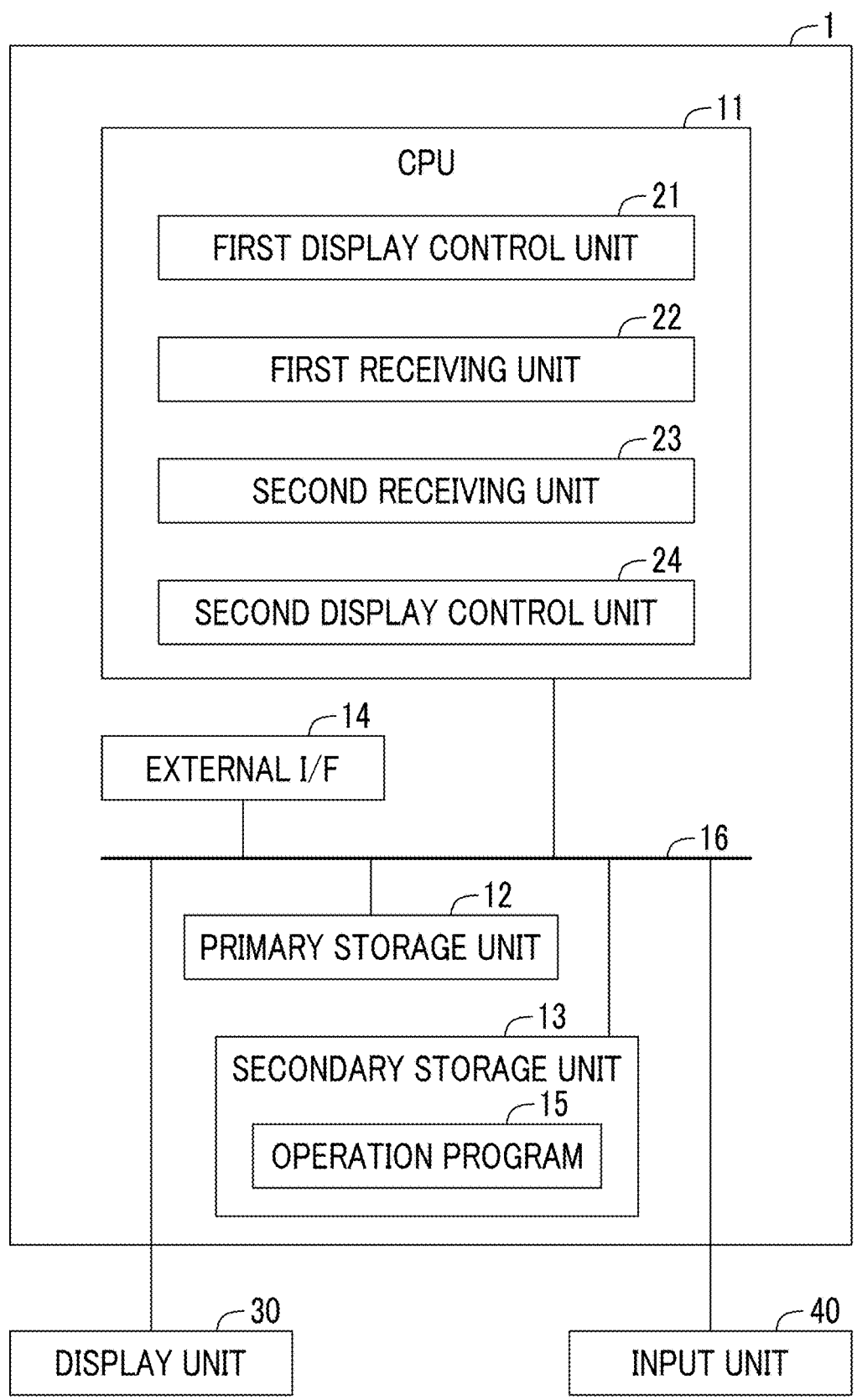
FIG. 2 is a block diagram schematically illustrating the configuration of a display control device according to a first embodiment of the present disclosure.

Next, the configuration of the display control device 1 will be described. FIG. 2 is a block diagram illustrating the configuration of a display control device 1 according to a first embodiment.

The display control device 1 is a computer comprising, for example, a central processing unit (CPU) 11, a primary memory 12, a secondary memory (storage unit) 13, an external interface (I/F) 14. The CPU 11 controls the entire display control device 1. The primary storage unit 12 is a volatile memory that is used as a work area in a case in which various programs are executed. An example of the primary memory 12 is a random access memory (RAM). The secondary memory 13 is a non-volatile memory in which various programs and various parameters are stored in advance. An embodiment of an operation program 15 of the display control device 1 according to the invention is installed in the secondary memory 13.

The operation program 15 is recorded on a recording medium, such as a digital versatile disc (DVD) or a compact disc read only memory (CD-ROM), is distributed, and is then installed in a computer from the recording medium. Alternatively, the operation program 15 may be stored in a storage device of a server computer connected to the network or a network storage such that it can be accessed from the outside, may be downloaded to the computer in response to a request from the outside, and may be installed.

The CPU 11 executes the operation program 15 to function as a first display control unit 21, a first receiving unit 22, a second receiving unit 23, and a second display control unit 24. An example of the secondary memory 13 is an electrically erasable programmable read-only memory (EEPROM) or a flash memory.

The external I/F 14 transmits and receives various kinds of information between the display control device 1 and the image storage server 3. The CPU 11, the primary memory 12, the secondary memory 13, and the external I/F 14 are connected to a bus line 16 which is a common path for each circuit to exchange data.

In addition, a display unit 30 and an input unit 40 are connected to the bus line 16. The display unit 30 is, for example, a liquid crystal display. The display unit 30 displays a display screen (see reference numeral 30M in FIG. 3) on which a display region and a selection region are displayed, which will be described below. The display unit 30 may be a touch panel and may also be used as the input unit 40. The input unit 40 comprises, for example, a mouse and a keyboard and receives various setting inputs by the user. The input unit 40 according to this embodiment functions as a mouse for inputting an operation of selecting a plurality of examination images received by the first receiving unit 22 and a mouse for inputting an operation of designating an arrangement direction in the display region which is received by the second receiving unit 23.

Figure 3:
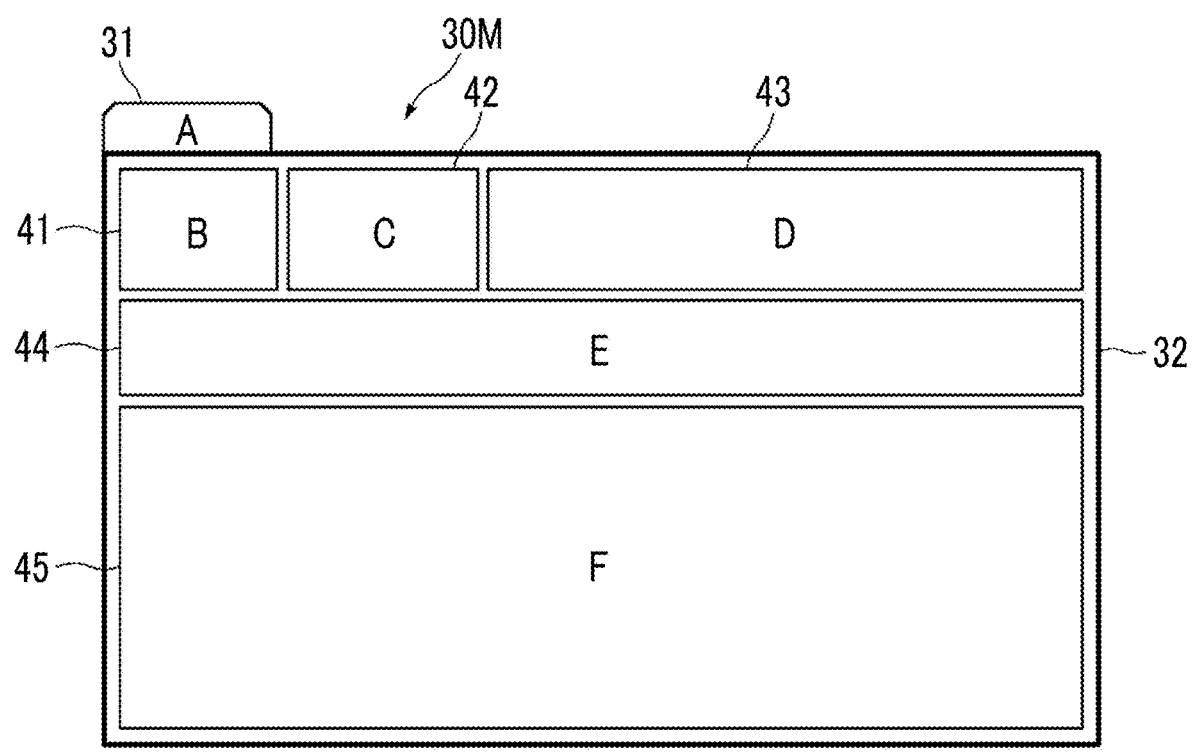
FIG. 3 is a diagram illustrating an example of a display screen according to an embodiment of the present disclosure.

The first display control unit 21 performs first display control to display, on the display screen, an examination image display region in which a plurality of examination images acquired for each examination are displayed and a thumbnail image display region in which a list of a plurality of thumbnail images obtained by reducing each of the plurality of examination images is displayed. The display screen 30M illustrated in FIG. 3 is an example of a display screen according to an embodiment of the present disclosure. The display screen 30M is an example of a graphical user interface (GUI) functioning as an operation screen that displays an examination image and various operation portions.

The display screen 30M includes a tab 31 represented by a region A, a patient information region 41 represented by a region B, an examination list region 42 represented by a region C, a thumbnail image display region 43 represented by a region D, a toolbar region 44 represented by a region E, and an image display region 45 represented by a region F as illustrated in FIG. 3. The image display region 45 corresponds to a display region according to the present disclosure and the thumbnail image display region 43 corresponds to a selection region according to the present disclosure.

Figure 4:
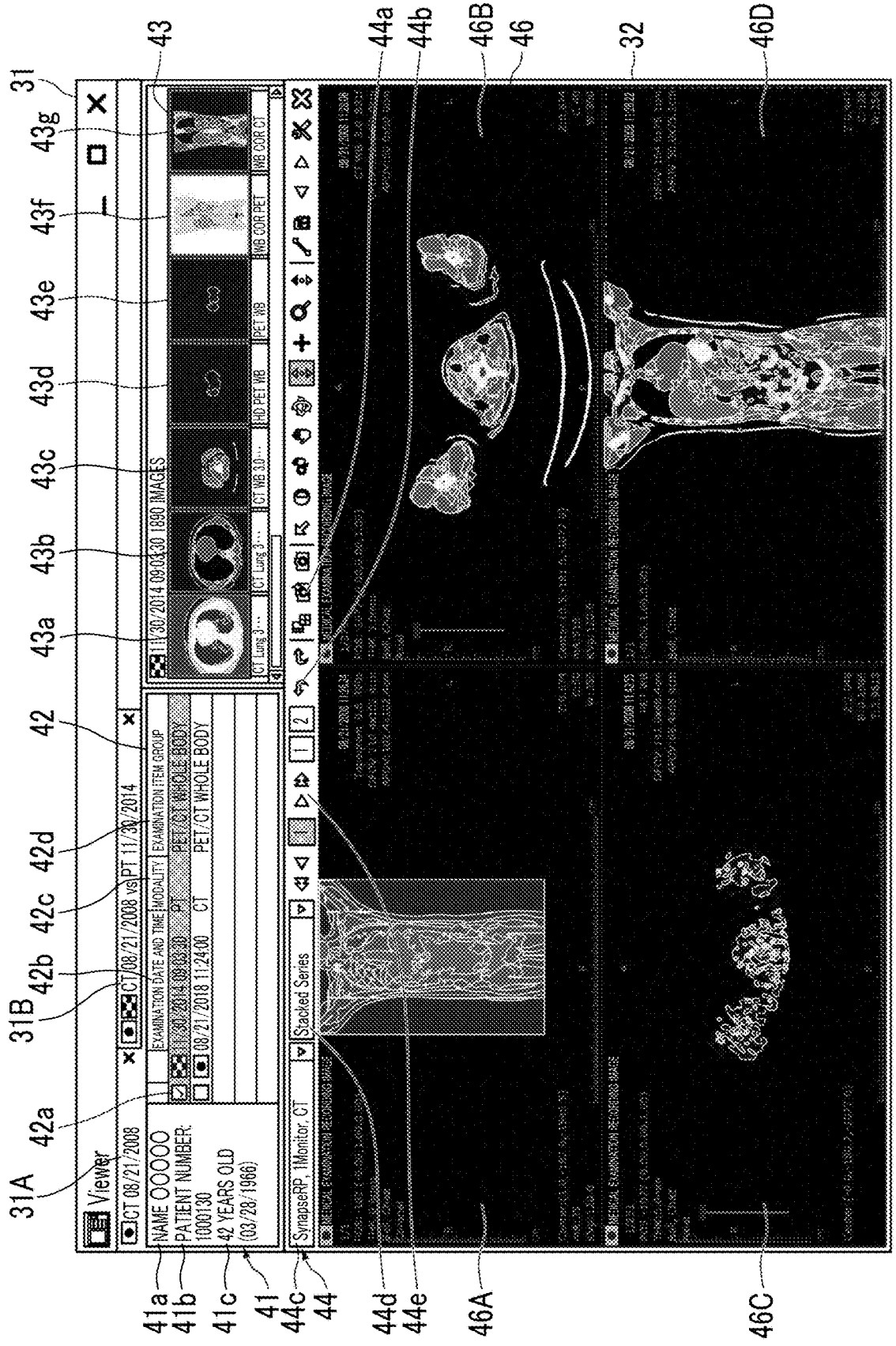
FIG. 4 is a diagram illustrating an example of the display of a display screen on a display unit according to an embodiment of the present disclosure.

The tab 31 is an operation portion for switching a viewer region 32. In the display screen 30M illustrated in FIG. 3, only one tab 31 is provided. However, in a case in which there are a plurality of tabs 31 (tabs 31A and 31B) as illustrated in FIG. 4, the viewer regions 32 corresponding to each tab 31 are provided. As illustrated in FIG. 3, the viewer region 32 corresponding to the tab 31 includes the patient information region 41, the examination list region 42, the thumbnail image display region 43, the toolbar region 44, and the image display region 45.

FIG. 4 is a diagram illustrating an example of display on the display screen 30M of the display unit 30 according to an embodiment of the present disclosure. As illustrated in FIG. 4, the tab 31A and the tab 31B adjacent to the tab 31A are displayed on the display screen 30M and the display aspect of the viewer region 32 corresponding to the tab can be set for each tab. In FIG. 4, the viewer region 32 corresponding to the tab 31A is displayed on the display screen 30M.

A patient's name 41a, a patient number 41b, and a patient's age and birthday 41c are displayed in the patient information region 41. An examination list including a check box 42a, an examination date and time 42b, a modality 42c, an examination item group 42d, and a mark 42e is displayed in the examination list region 42.

The thumbnail image display region 43 is a region in which a thumbnail image obtained by reducing the examination image is displayed. In this embodiment, the thumbnail image display region 43 includes thumbnail regions 43a to 43g in which seven thumbnail images are displayed. The thumbnail images obtained by reducing the examination images acquired in the examination in which the check box 42a has been checked are displayed in the thumbnail regions 43a to 43g. In a case in which the number of examination images acquired in the examination is greater than seven, the first display control unit 21 operates, for example, a scroll bar illustrated in FIG. 4 to change the displayed thumbnail image.

Various command buttons, such as a snapshot button 44a, a return button 44b, a first pull-down menu 44c for selecting an arrangement configuration of the display screen 30M, and a second pull-down menu 44d for selecting the type of examination image acquired in one examination, are displayed in the toolbar region 44. In this embodiment, in a case in which the above-mentioned command button is pressed, a command associated with the pressed command button is input. Specifically, in a case in which the snapshot button 44a is pressed, a snapshot command is input. In a case in which the return button 44b is pressed, a command to return the image display region 45 to the previous display state is input.

The image display region 45 is a display region in which the examination images acquired for each examination are displayed. A plurality of display frames 46 that can be laid out as the display positions of a plurality of examination images are arranged in a grid shape in the image display region 45. In this embodiment, a total of four display frames 46A to 46D are arranged in two rows and two columns (2×2) and the examination images selected by the user are laid out and displayed in the four display frames 46A to 46D.

Figure 5:
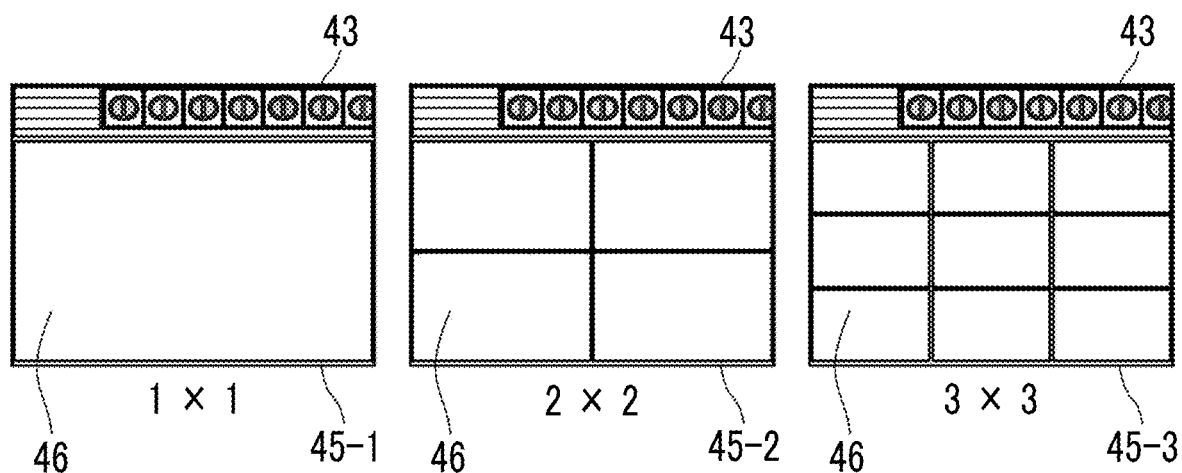
FIG. 5 is a diagram illustrating an example of the configuration of an image display region according to the first embodiment of the present disclosure.

In the image display region 45, the number of display frames 46 can be set in advance by the user. FIG. 5 is a diagram illustrating an example of the configuration of the image display region 45 according to an embodiment of the present disclosure. For example, as illustrated in FIG. 5, the user selects any arrangement configuration in advance from arrangement configurations, such as an image display region 45-1 in which the display frames 46 are arranged in a 1×1 grid shape, an image display region 45-2 in which the display frames 46 are arranged in a 2×2 grid shape, and an image display region 45-3 in which the display frames 46 are arranged in a 3×3 grid shape. The arrangement configurations of the display frames 46 in the image display region 45 are stored as templates in the primary memory 12 and the user selects the arrangement configuration using, for example, the first pull-down menu 44c. In the image display region 45, a frame line indicating the outer frame of the display frame 46 may be displayed such that the user can easily recognize the arrangement configuration of the display frame 46 or the frame line may not be displayed.

Figure 6:
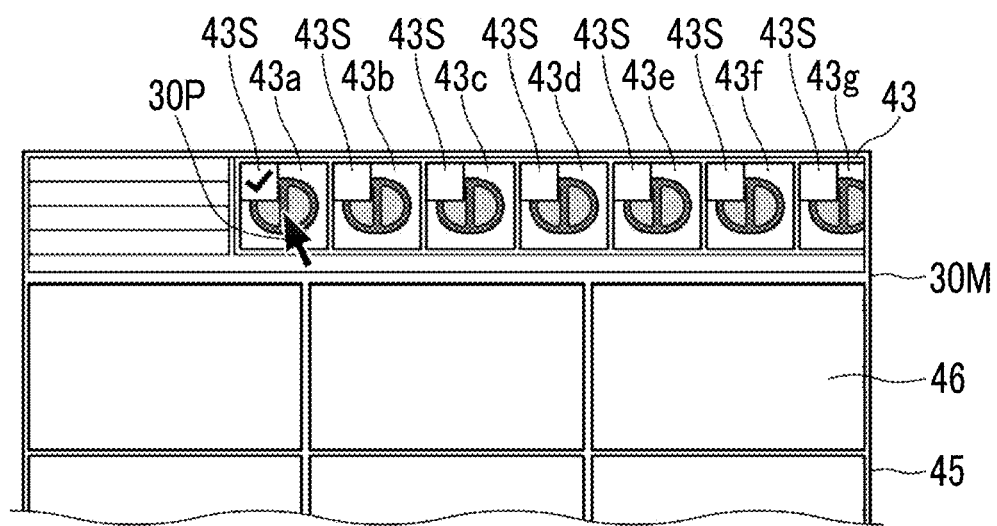
FIG. 6 is a diagram illustrating a thumbnail image selection operation.

Returning to FIG. 2, the first receiving unit 22 receives an operation of selecting a plurality of thumbnail images from the thumbnail image display region 43 to select a plurality of examination images corresponding to the plurality of thumbnail images. FIG. 6 is a diagram illustrating a thumbnail image selection operation.

As illustrated in FIG. 6, check boxes 43S are displayed on the thumbnail images displayed in each of the thumbnail regions 43a to 43g in the thumbnail image display region 43. In a case in which the user operates the input unit 40 to move a pointer 30P and checks the check box 43S, the checked thumbnail image is selected. In a case in which a plurality of check boxes 43S are checked, a plurality of thumbnail images are selected. The first receiving unit 22 receives an examination image corresponding to the selected thumbnail image as the selected examination image.

In a state in which a plurality of thumbnail images are selected in the thumbnail image display region 43 and before four examination images are laid out in four display frames 46A to 46D of the display screen 30M, the second receiving unit 23 receives an operation of designating the arrangement direction of the selected four examination images in the image display region 45. The operation of designating the arrangement direction will be described in detail below.

The second display control unit 24 performs second display control to lay out the selected four examination images in the four display frames 46A to 46D in the designated arrangement direction and to display the four examination images laid out in the four display frames 46A to 46D on the display screen 30M.

Figure 7:
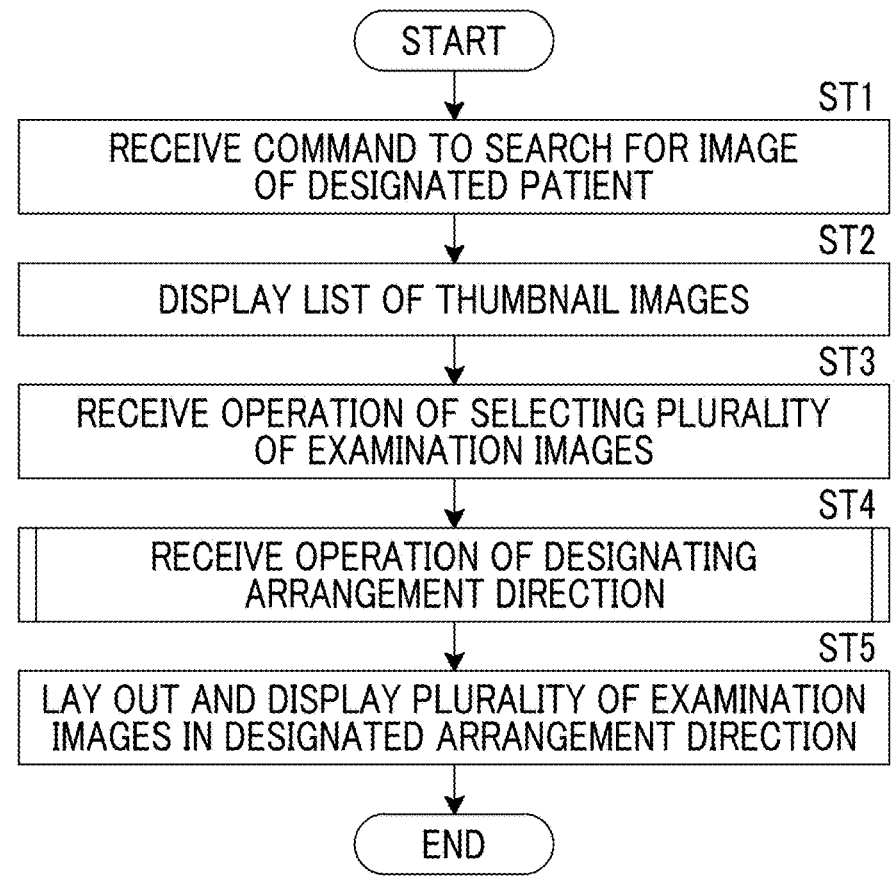
FIG. 7 is a flowchart illustrating a process performed in the first embodiment of the present disclosure.

Next, a process performed in this embodiment will be described. FIG. 7 is a flowchart illustrating a process performed in the first embodiment of the present disclosure. In this embodiment, in the image display region 45, display frames 46A to 46I arranged in a 3×3 grid shape are set in advance.

First, the first display control unit 21 receives a command to search for the image of a designated patient (Step ST1). Specifically, as illustrated in FIG. 4, in a case in which the user inputs a patient ID using the input unit 40, the first display control unit 21 displays patient information corresponding to the input patient ID in the patient information region 41 of the display screen 30M. In addition, the first display control unit 21 displays a list of the examinations received by the input patient ID in the examination list region 42. Further, in a case in which the user checks the check box 42a of the examination list displayed in the examination list region 42, the first display control unit 21 searches for a plurality of examination images acquired on the checked examination date in the image storage server 3 and acquires the plurality of examination images.

In this embodiment, the first display control unit 21 acquires a plurality of examination images from the image storage server 3. However, the technology of the present disclosure is not limited thereto. The first display control unit 21 may acquire the examination images of the corresponding patient in advance from the image storage server 3, store the acquired examination images in the storage unit, search for a plurality of examination images acquired on the checked examination date from the plurality of examination images stored in the storage unit, and acquire the plurality of examination images. In addition, in this embodiment, the example in which the first display control unit 21 also functions as an image acquisition unit that acquires an examination image from the image storage server 3 has been described. However, of course, the image acquisition unit may be provided separately from the first display control unit 21.

Then, the first display control unit 21 displays a list of a plurality of thumbnail images obtained by reducing the plurality of acquired examination images in the thumbnail image display region 43 as illustrated in FIG. 4 (Step ST2).

Then, the first receiving unit 22 receives an operation of selecting a plurality of thumbnail images from the list of the thumbnail images displayed in the thumbnail image display region 43 to select a plurality of examination images corresponding to the plurality of thumbnail images (Step ST3). In a case in which the user operates the input unit 40 to move the pointer 30P and checks the check boxes 43S of a plurality of thumbnail images that the user wants to select (see FIG. 6), the plurality of checked thumbnail images are selected. The first receiving unit 22 receives a plurality of examination images corresponding to the plurality of selected thumbnail images.

Figure 8:
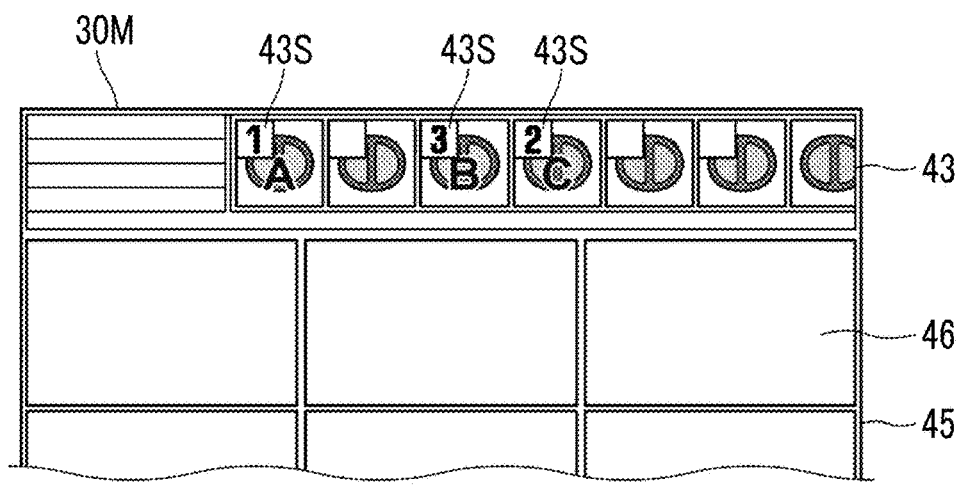
FIG. 8 is a diagram illustrating reception of a selection order of a plurality of thumbnail images.

FIG. 8 is a diagram illustrating the reception of the selection order of a plurality of thumbnail images. In this embodiment, the first receiving unit 22 receives the selection order in which the thumbnail images are selected. As illustrated in FIG. 8, numbers indicating the selection order in which the check boxes 43S are checked are displayed in the check boxes 43S. For example, in FIG. 8, the first receiving unit 22 receives the selection order of a thumbnail image A, a thumbnail image C, and a thumbnail image B.

Returning to FIG. 7, in a state in which a plurality of thumbnail images are selected and before the examination images are laid out in a plurality of display frames 46, the second receiving unit 23 receives an operation of designating the arrangement direction of the plurality of selected examination images in the image display region 45 (Step ST4).

Figure 9:
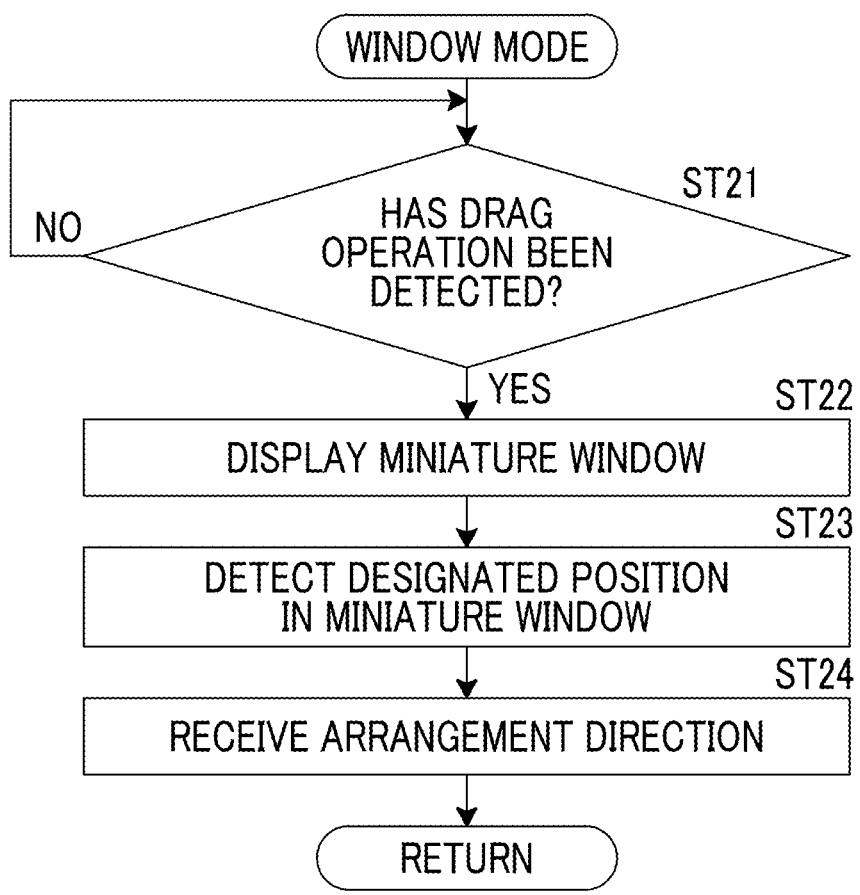
FIG. 9 is a flowchart illustrating a series of processes in a window mode for receiving an operation of designating an arrangement direction.

FIG. 9 is a flowchart illustrating a series of processes in a window mode that receives the operation of designating the arrangement direction. As illustrated in FIG. 9, first, the second receiving unit 23 detects whether or not a drag operation of dragging a plurality of thumbnail images selected in the thumbnail image display region 43 from the thumbnail image display region 43 has been performed (Step ST21). The detection of the drag operation can be performed, for example, by detecting whether or not the mouse has been moved in a state in which a left button of the mouse is pressed on any region of the plurality of selected thumbnail images. In a case in which the detection result in Step ST21 is "NO" (Step ST21; NO), the process in Step ST21 is repeated until the second receiving unit 23 detects the drag operation.

Figure 10:
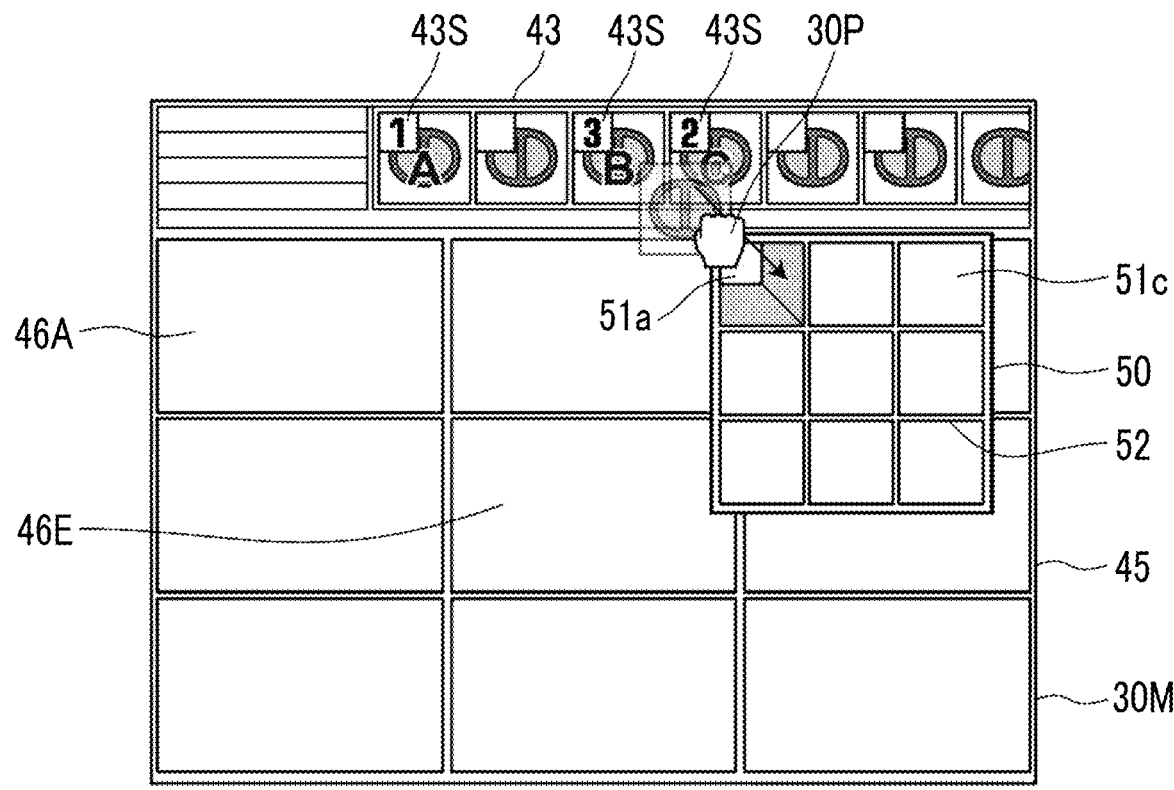
FIG. 10 is a diagram illustrating the display of a miniature window.

On the other hand, in a case in which the detection result in Step ST21 is "YES" (Step ST21; YES), the first display control unit 21 displays a miniature window 50 on the display screen 30M (Step ST22). The miniature window 50 is used as a designation window for designating the arrangement direction of the plurality of selected examination images. The miniature window 50 is also used as a designation window for designating a display frame at the head (first display frame) among the display frames in which the plurality of selected examination images are arranged. FIG. 10 is a diagram illustrating the display of the miniature window.

As illustrated in FIG. 10, the miniature window 50 is a region in which display frames obtained by reducing the grid-shaped arrangement of the plurality of display frames 46, that is, miniature display frames 51 are arranged in a grid shape and is displayed in the display screen 30M separately from the image display region 45. In this embodiment, since nine display frames 46A to 46I are set in a 3×3 grid shape in the image display region 45, nine miniature display frames 51*a* to 51*i* are set in a 3×3 grid shape in the miniature window 50. In the miniature window 50, a frame line 52 of each of the miniature display frames 51*a* to 51*i* is displayed.

The miniature window 50 is disposed in the vicinity of the thumbnail image display region 43.

In a case in which the miniature window 50 is displayed on the display screen 30M, the second receiving unit 23 detects a designated position in the miniature window 50 (Step ST23). The second receiving unit 23 receives the arrangement direction of the plurality of selected examination images on the basis of the detected designated position (Step ST24). In Step ST24, the second receiving unit 23 receives the designation of the first display frame of the plurality of selected examination images on the basis of the detected designated position, in addition to the arrangement direction.

As illustrated in FIG. 10, the second receiving unit 23 detects, as the designated position, a position where the plurality of thumbnail images selected in the thumbnail image display region 43 are dragged in the direction of an arrow in FIG. 10 and then dropped.

First, the second receiving unit 23 determines the first display frame in the image display region 45 on the basis of the designated position detected in the miniature window 50. In FIG. 10, the designated position is included in the upper left miniature display frame 51*a* in the miniature window 50. The miniature display frame 51*a* corresponds to the upper left display frame 46A in the image display region 45. The second receiving unit 23 sets the display frame 46A as the first display frame of the plurality of laid-out examination images on the basis of the correspondence relationship between the position of the miniature display frame 51*a* in the miniature window 50 and the position of the display frame 46A in the image display region 45. Therefore, the second receiving unit 23 receives an operation of designating the first display frame of the plurality of laid-out examination images.

Then, the second receiving unit 23 receives the arrangement direction of the plurality of selected examination images on the basis of the detected designated position. Specifically, the second receiving unit 23 receives the designation of the vertical direction or the horizontal direction as the arrangement direction of the plurality of examination images.

FIGS. 11 to 16 are diagrams illustrating examples of the arrangement direction based on the designated position in the display frame.

In this embodiment, as illustrated in FIGS. 11 to 16, a horizontal direction designation region 51R for designating the horizontal direction (the direction of an arrow X in FIGS. 11 to 16) as the arrangement direction and a vertical direction designation region 51D for designating the vertical direction (the direction of an arrow Y in FIGS. 11 to 16) as the arrangement direction are set in the miniature display frame 51. The horizontal direction designation region 51R is a region on the right side of a vertical line passing through the center in the miniature display frame 51 and a region above a diagonal line connecting the upper left vertex and the lower right vertex. Further, the vertical direction designation region 51D is a region below a horizontal line passing through the center in the miniature display frame 51 and a region on the left side of a diagonal line connecting the upper left vertex and the lower right vertex. The horizontal direction designation region 51R and the vertical direction designation region 51D are displayed in each miniature display frame 51 in a different aspect (for example, in a different color) from other regions.

Figure 11:
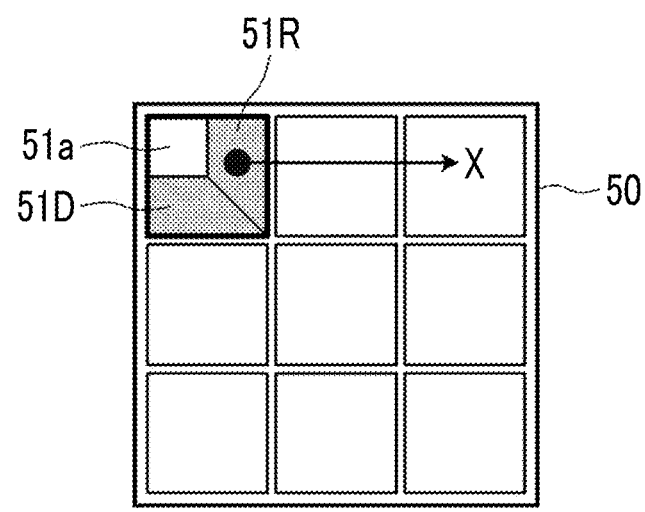
FIG. 11 is a diagram illustrating an example of the arrangement direction based on a designated position in a display frame.

In the example illustrated in FIG. 11, the second receiving unit 23 detects a drop operation in the horizontal direction designation region 51R in the upper left miniature display frame 51*a* and detects the horizontal direction designation region 51R of the upper left miniature display frame 51*a* as the designated position. Then, the second receiving unit 23 sets the upper left display frame 46A (see FIG. 10) of the image display region 45 corresponding to the upper left miniature display frame 51*a* as the first display frame of the plurality of laid-out examination images and receives an operation of designating the horizontal direction as the arrangement direction.

Figure 12:
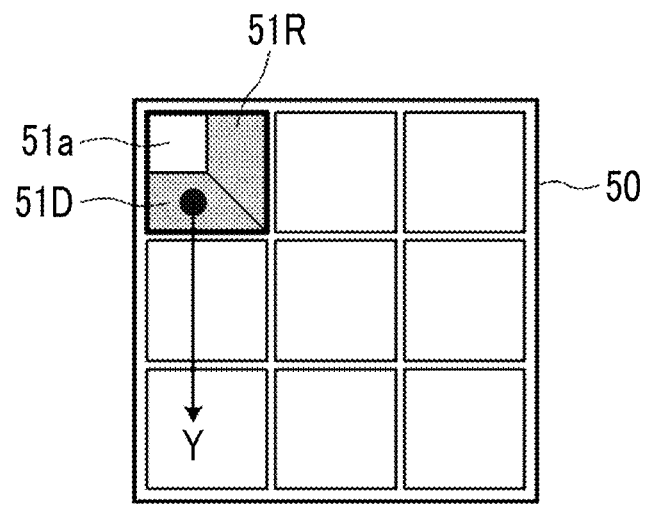
FIG. 12 is a diagram illustrating an example of the arrangement direction based on a designated position in the display frame.

As illustrated in FIG. 12, in a case in which a drop operation is detected in the vertical direction designation region 51D in the upper left miniature display frame 51*a*, the vertical direction designation region 51D of the upper left miniature display frame 51*a* is detected as the designated position. Then, the second receiving unit 23 sets the upper left display frame 46A (see FIG. 10) of the image display region 45 corresponding to the upper left miniature display frame 51*a* as the first display frame of the plurality of laid-out examination images and receives an operation of designating the vertical direction as the arrangement direction.

In a case in which the number of examination images to be laid out does not fit in one line which is a row in the horizontal direction or one line which is a column in the vertical direction, the second receiving unit 23 changes the line such that the remaining examination images which do not fit in one line are laid out on an adjacent line. FIGS. 13 to 16 illustrate examples in which a plurality of examination images are arranged on a plurality of lines.

A case in which the second receiving unit 23 detects a drop operation in the horizontal direction designation region 51R in the upper left miniature display frame 51*a* as illustrated in FIG. 11, that is, a case in which the second receiving unit 23 receives the operation of designating the horizontal direction as the arrangement direction is considered. In a case in which the number of selected examination images is greater than the number of miniature display frames 51 and display frames 46 in the horizontal line (row) corresponding to the designated position, the second receiving unit 23 changes the line. That is, as illustrated in FIG. 13, the remaining examination images that do not fit in one row are arranged from the left end of the next row to the right.

Figure 13:
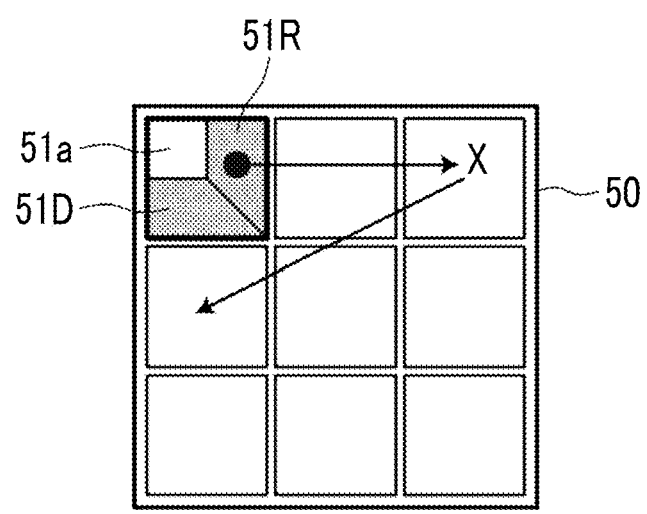
FIG. 13 is a diagram illustrating an example of the arrangement direction based on a designated position in the display frame.
Figure 14:
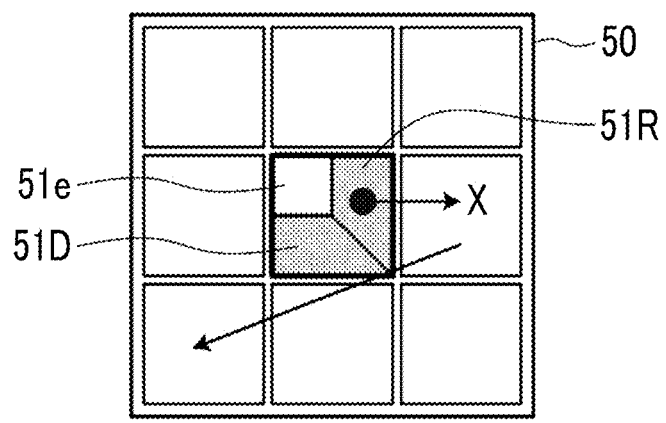
FIG. 14 is a diagram illustrating an example of the arrangement direction based on a designated position in the display frame.

In addition, as illustrated in FIG. 14, in a case in which a drop operation is detected in the horizontal direction designation region 51R in the central miniature display frame 51*e*, the process is basically the same as that illustrated in FIG. 13 except that the first display frame is different. That is, in a case in which the number of selected examination images is greater than the number of miniature display frames 51 and display frames 46 from the center to the right end, the line is changed as illustrated in FIG. 14. Then, the remaining examination images are arranged from the left end of the next row to the right.

Figure 15:
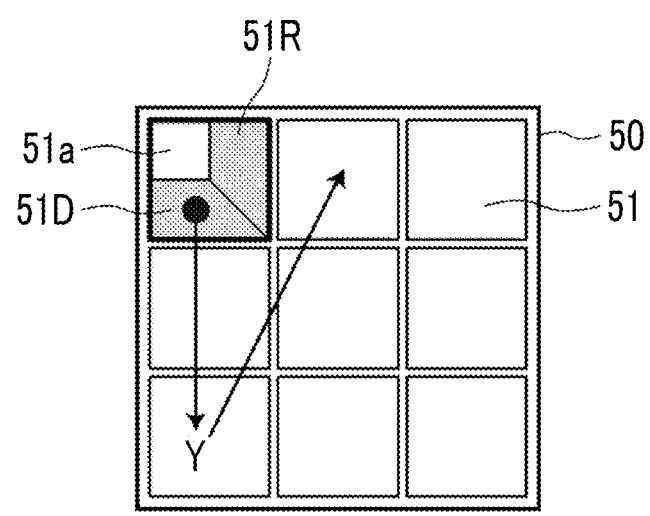
FIG. 15 is a diagram illustrating an example of the arrangement direction based on a designated position in the display frame.

Further, in a case in which a drop operation is detected in the vertical direction designation region 51D in the upper left miniature display frame 51*a* as illustrated in FIG. 12, that is, in a case in which the second receiving unit 23 receives the operation of designating the vertical direction as the arrangement direction, the second receiving unit 23 performs a line break, for example, as illustrated in FIG. 15. That is, in a case in which the number of selected examination images is greater than the number of miniature display frames 51 and display frames 46 in the vertical line (column) corresponding to the designated position, the second receiving unit 23 arranges the remaining examination images that do not fit in one column from the top of the next column to the bottom as illustrated in FIG. 15.

Figure 16:
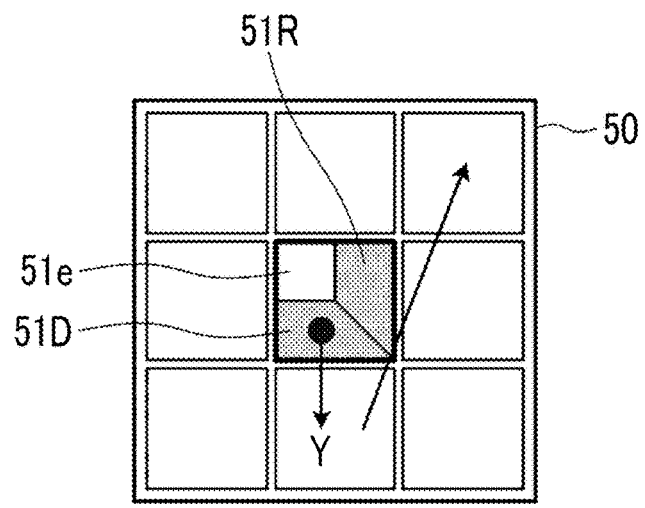
FIG. 16 is a diagram illustrating an example of the arrangement direction based on a designated position in the display frame.

Also, as illustrated in FIG. 16, in a case in which a drop operation is detected in the vertical direction designation region 51D in the central miniature display frame 51e, the process is basically the same as that illustrated in FIG. 14 except that the first display frame is different. That is, in a case in which the number of selected examination images is greater than the number of miniature display frames 51 and display frames 46 from the center to the lower end, the line is changed as illustrated in FIG. 16. Then, the remaining examination images are arranged from the top of the next row to the bottom.

Figure 17:
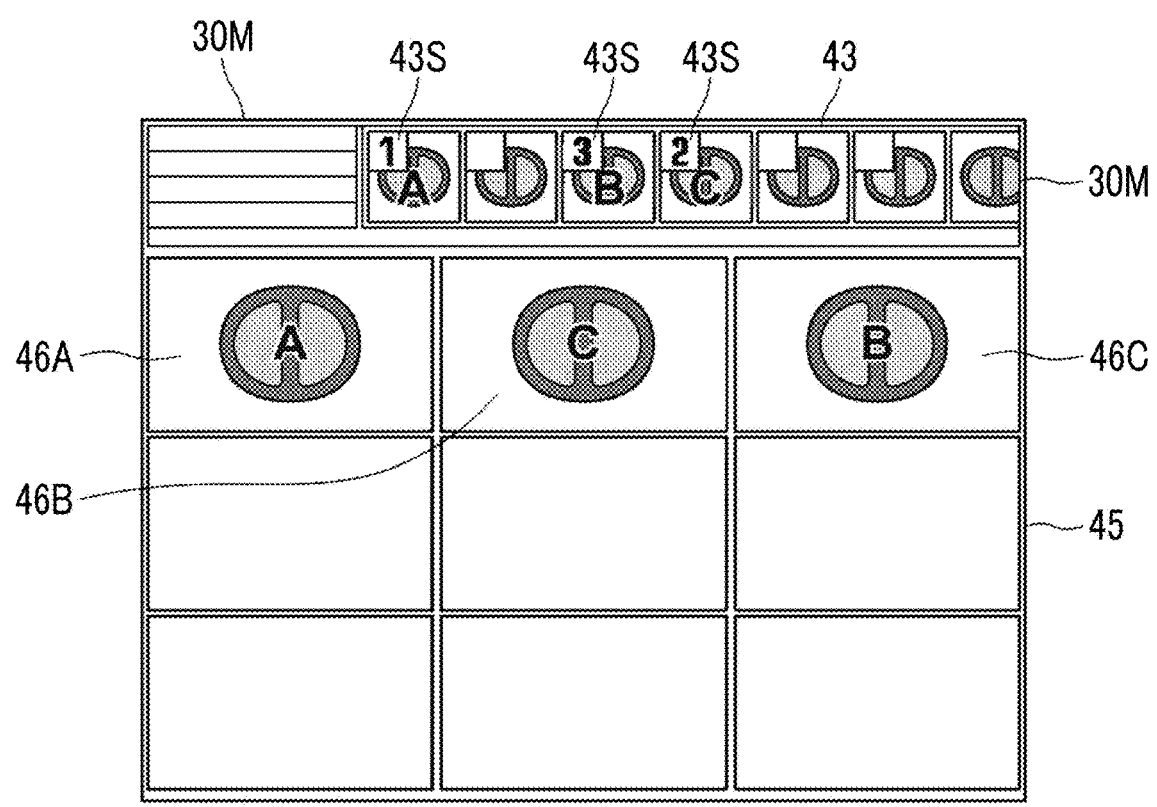
FIG. 17 is a diagram illustrating an example of the display of a display screen.

Returning to FIG. 7, in a case in which the second receiving unit 23 receives an operation of designating the arrangement direction (Step ST4), the second display control unit 24 lays out a plurality of examination images in a plurality of display frames 46 of the image display region 45 in the designated arrangement direction and displays the plurality of examination images laid out in the plurality of display frames 46 on the display screen 30M (Step ST5). FIG. 17 is a diagram illustrating an example of the display of the display screen 30M in a case in which the upper left display frame 46A is designated as the first display frame and the horizontal direction is designated as the arrangement direction as illustrated in FIGS. 10 and 11.

As illustrated in FIG. 17, the second display control unit 24 lays out three examination images received by the first receiving unit 22 on the basis of the arrangement order of numbers assigned to the thumbnail images corresponding to each examination image. That is, the examination images are laid out in the order of the examination image A, the examination image C, and the examination image B. In addition, the second display control unit 24 lays out the examination images from the display frame 46A set as the first display frame in the horizontal direction which is the arrangement direction received by the first receiving unit 22. Specifically, the examination image A is laid out in the display frame 46A, the examination image C is laid out in the display frame 46B, and the examination image B is laid out in the display frame 46C.

The second display control unit 24 displays the examination images A to C laid out in the display frames 46A to 46C on the display screen 30M.

As described above, according to the first embodiment, in a case in which a plurality of examination images are laid out in a plurality of display frames 46 arranged in the image display region 45, the designation of the arrangement direction is received and a plurality of examination images are laid out in the designated arrangement direction. Therefore, it is possible to lay out a plurality of examination images in a desired arrangement direction with a simple operation, as compared to a case in which the layout position of each examination image is designated.

In addition, according to the first embodiment, in a case in which the second receiving unit 23 receives the operation of designating the arrangement direction, the first display frame is set. Therefore, the user can designate not only the arrangement direction but also the position at which the arrangement of the examination images is started. Therefore, the designation of the arrangement direction of a plurality of examination images and the designation of the position of the first display frame can be performed by one operation and thus user convenience is improved.

Further, according to the first embodiment, the arrangement order desired by the user can be determined by the selection order of the thumbnail images. Therefore, it is possible to reduce the time and effort required for setting the arrangement order and user operability is improved.

Furthermore, according to the first embodiment, the operation of designating the arrangement direction and the operation of designating the position of the first display frame are received by a drag and drop method. Therefore, the user can perform designation with one operation and operability is improved. In this embodiment, the example which a designation operation is received by a drag and drop method has been described. However, the technology of the present disclosure is not limited thereto. The designation operation may be received by aspects other than the drag and drop method. For example, after selecting a thumbnail image, the user may perform designation by clicking a desired position using the pointer 30P displayed on the display screen 30M.

In the first embodiment, the miniature window 50 is displayed on the display screen 30M at the timing when the drag operation is detected, that is, at the timing when the drag operation is started. However, the technology of the present disclosure is not limited thereto. For example, the miniature window 50 may be displayed on the display screen 30M immediately before the drag operation is started, specifically, at the timing when the left button of the mouse is pressed on any region of a plurality of thumbnail images.

In the first embodiment, in the image display region 45, a plurality of display frames 46 that can be laid out as the display positions of a plurality of examination images are arranged in a grid shape. In the technology of the present disclosure, the term "arrangement in a grid shape" includes, for example, a case in which the display frames 46 are arranged in one row and four columns (1×4) or in four rows and one column (4×1).

Figure 18:
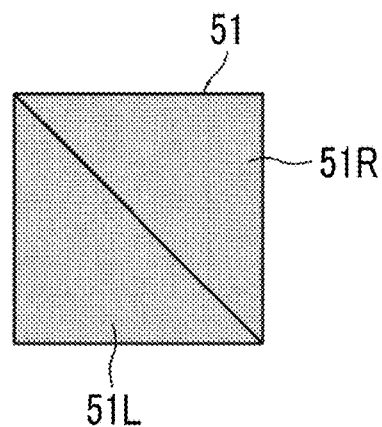
FIG. 18 is a diagram illustrating an example of a horizontal direction designation region and a vertical direction designation region set in a miniature display frame.
Figure 19:
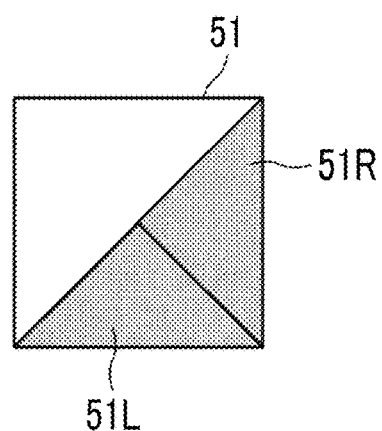
FIG. 19 is a diagram illustrating an example of the horizontal direction designation region and the vertical direction designation region set in the miniature display frame.
Figure 20:
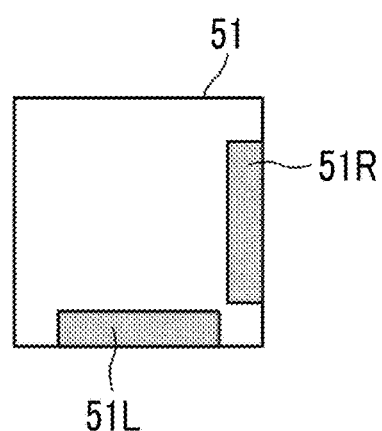
FIG. 20 is a diagram illustrating an example of the horizontal direction designation region and the vertical direction designation region set in the miniature display frame.

Further, in the first embodiment, the horizontal direction designation region 51R and the vertical direction designation region 51D are set in the miniature display frame 51 as illustrated in FIGS. 11 to 16. However, the technology of the present disclosure is not limited thereto. For example, instead of the region, any one of four sides forming the miniature display frame 51 may be used. Specifically, the horizontal direction designation region may be the right side among the four sides forming the miniature display frame 51 and the vertical direction designation region may be the lower side among the four sides. In addition, the inside of the miniature display frame 51 may be divided into a plurality of small regions and any one of the divided small regions may be designated. FIGS. 18 to 20 are diagrams illustrating examples of the horizontal direction designation region 51R and the vertical direction designation region 51D set in the miniature display frame 51.

As illustrated in FIG. 18, a region above a diagonal line connecting the upper left vertex and the lower right vertex of the miniature display frame 51 may be set as the horizontal direction designation region 51R and a region below the diagonal line may be set as the vertical direction designation region 51D.

As illustrated in FIG. 19, in a region below a diagonal line connecting the lower left vertex and the upper right vertex of the miniature display frame 51, a region above a line connecting the lower right vertex and the center of the miniature display frame 51 may be set as the horizontal direction designation region 51R and a region below the line may be set as the vertical direction designation region 51D.

As illustrated in FIG. 20, in the miniature display frame 51, a rectangular region including a part of the right side among four sides forming the miniature display frame 51 may be set as the horizontal direction designation region 51R and a rectangular region including a part of the lower side may be set as the vertical direction designation region 51D.

Figure 21:
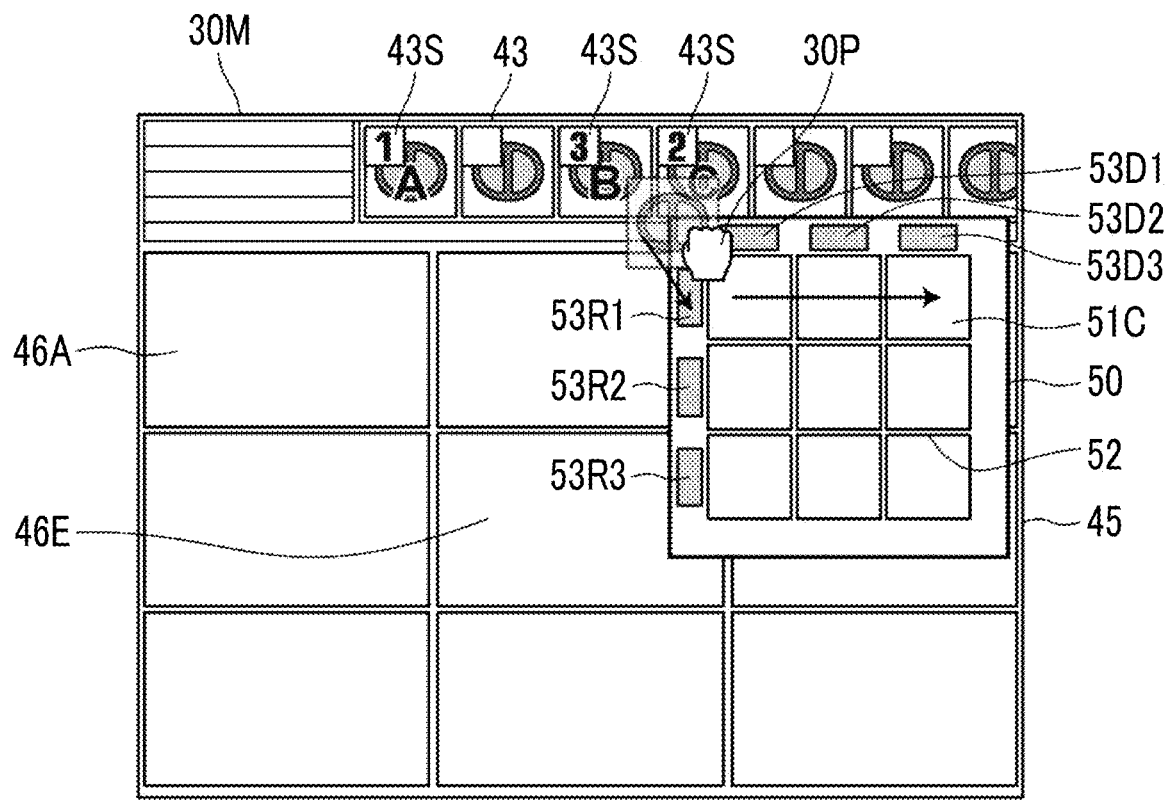
FIG. 21 is a diagram illustrating Modification Example 1 of the miniature window according to the first embodiment of the present disclosure.

Next, Modification Example 1 of the first embodiment will be described. In the following embodiments, since configurations are the same as those in the first embodiment except a position designation operation, only the position designation operation will be described. FIG. 21 is a diagram illustrating Modification Example 1 of the miniature window according to the first embodiment of the present disclosure and FIG. 22 is a diagram illustrating an example of the arrangement direction based on the designated position in the miniature window illustrated in FIG. 21.

In Modification Example 1, the configuration of the miniature window 50 is different from that in the first embodiment. As illustrated in FIGS. 21 and 22, the miniature window 50 as a designation window according to Modification Example 1 has a frame region 53 that is provided in an outer peripheral portion surrounding nine miniature display frames 51a to 51i. In the frame region 53, a first horizontal direction designation region 53R1 having a rectangular shape is provided on the left side of a first row of the miniature display frames 51, a second horizontal direction designation region 53R2 having a rectangular shape is provided on the left side of a second row, and a third horizontal direction designation region 53R3 having a rectangular shape is provided on the left side of a third row.

Further, in the frame region 53, a first vertical direction designation region 53D1 having a rectangular shape is provided above the leftmost column of the miniature display frames 51, a second vertical direction designation region 53D2 having a rectangular shape is provided above the middle column, and a third vertical direction designation region 53D3 having a rectangular shape is provided above the rightmost column. The designation regions 53R1, 53R2, 53R3, 53D1, 53D2, and 53D3 function as operation portions for the second receiving unit 23 to receive a designation operation.

Figure 22:
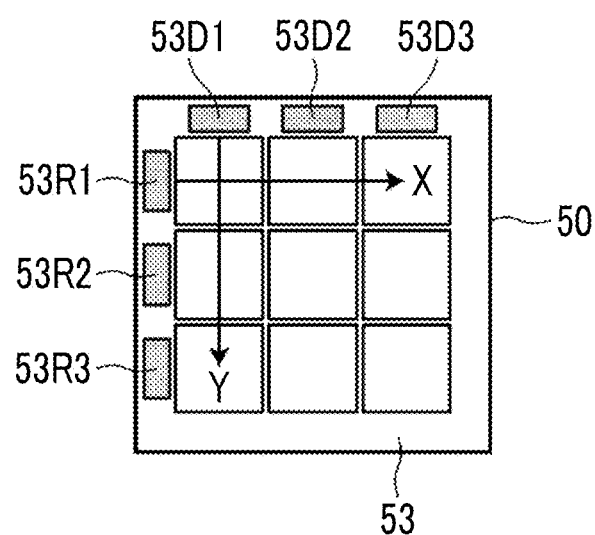
FIG. 22 is a diagram illustrating an example of the arrangement direction based on a designated position in the miniature window illustrated in FIG. 21.

As illustrated in FIG. 22, in a case in which the second receiving unit 23 receives a designation operation in the first horizontal direction designation region 53R1, the right horizontal direction (in FIG. 22, the X direction) from the leftmost miniature display frame 51 in the first row is set as the arrangement direction. Then, the second display control unit 24 lays out the selected three examination images in the selected order in the right horizontal direction from the display frame 46 of the image display region 45 corresponding to the leftmost miniature display frame 51 in the first row.

Similarly, in a case in which the second receiving unit 23 receives a designation operation in the second horizontal direction designation region 53R2, the right horizontal direction from the leftmost miniature display frame 51 in the second row is set as the arrangement direction. Then, the second display control unit 24 lays out the selected three examination images in the selected order in the right horizontal direction from the display frame 46 of the image display region 45 corresponding to the leftmost miniature display frame 51 in the second row. In addition, in a case in which the second receiving unit 23 receives a designation operation in the third horizontal direction designation region 53R3, the right horizontal direction from the leftmost miniature display frame 51 in the third row is set as the arrangement direction. Then, the second display control unit 24 lays out the selected three examination images in the selected order in the right horizontal direction from the display frame 46 of the image display region 45 corresponding to the leftmost miniature display frame 51 in the third row.

Further, in a case in which the second receiving unit 23 receives a designation operation in the first vertical direction designation region 53D1 as illustrated in FIG. 22, the downward direction (in FIG. 22, the Y direction) from the leftmost miniature display frame 51 in the first column is set as the arrangement direction. Then, the second display control unit 24 lays out the selected three examination images in the selected order in the downward direction from the display frame 46 of the image display region 45 corresponding to the leftmost miniature display frame 51 in the first column.

Similarly, in a case in which the second receiving unit 23 receives a designation operation in the second vertical direction designation region 53D2, the downward direction from the uppermost miniature display frame 51 in the second column from the left is set as the arrangement direction. Then, the second display control unit 24 lays out the selected three examination images in the selected order in the downward direction from the display frame 46 of the image display region 45 corresponding to the uppermost miniature display frame 51 in the second column from the left. Further, in a case in which the second receiving unit 23 receives a designation operation in the third vertical direction designation region 53D3, the downward direction from the uppermost miniature display frame 51 in the third column is set as the arrangement direction. Then, the second display control unit 24 lays out the selected three examination images in the selected order in the downward direction from the display frame 46 of the image display region 45 corresponding to the uppermost miniature display frame 51 in the third column.

Figure 23:
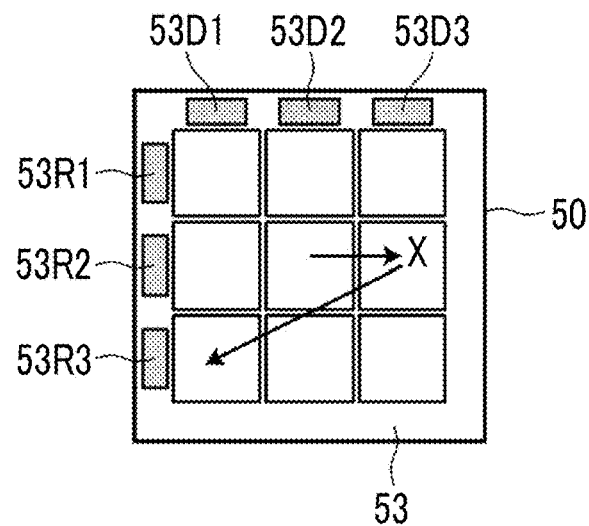
FIG. 23 is a diagram illustrating another example of the arrangement direction based on a designated position in the miniature window illustrated in FIG. 21.

In Modification Example 1, in some cases, the miniature display frame 51 other than the frame region 53 in which the operation portion for a designation operation is disposed is designated. In the exceptional case, for example, the arrangement direction is processed as follows in accordance with the preset content. For example, a case in which the second receiving unit 23 receives a designation operation in the central miniature display frame 51 other than the frame region 53 as illustrated in FIG. 23 is considered. In this case, a preset direction, for example, the horizontal direction is set as the arrangement direction. Then, the second display control unit 24 sets a display frame 46 of the image display region 45 corresponding to the central miniature display frame 51 as the first display frame and lays out the selected three examination images in the selected order in the right horizontal direction from the first display frame. In addition, in a case in which the number of display frames 46 from the display frame 46 to the right end of the image display region 45 is less than the number of selected examination images, the arrangement is turned back from the display frame 46 at the right end and the examination images are laid out from the first display frame 46 in the next row, as illustrated in FIG. 23.

In Modification Example 1, the designation region is provided on the frame region 53. However, the technology of the present disclosure is not limited thereto. For example, the designated position may be on the line of the outer frame of the miniature window 50 or may be an outer region adjacent to the outer frame.

Figure 24:
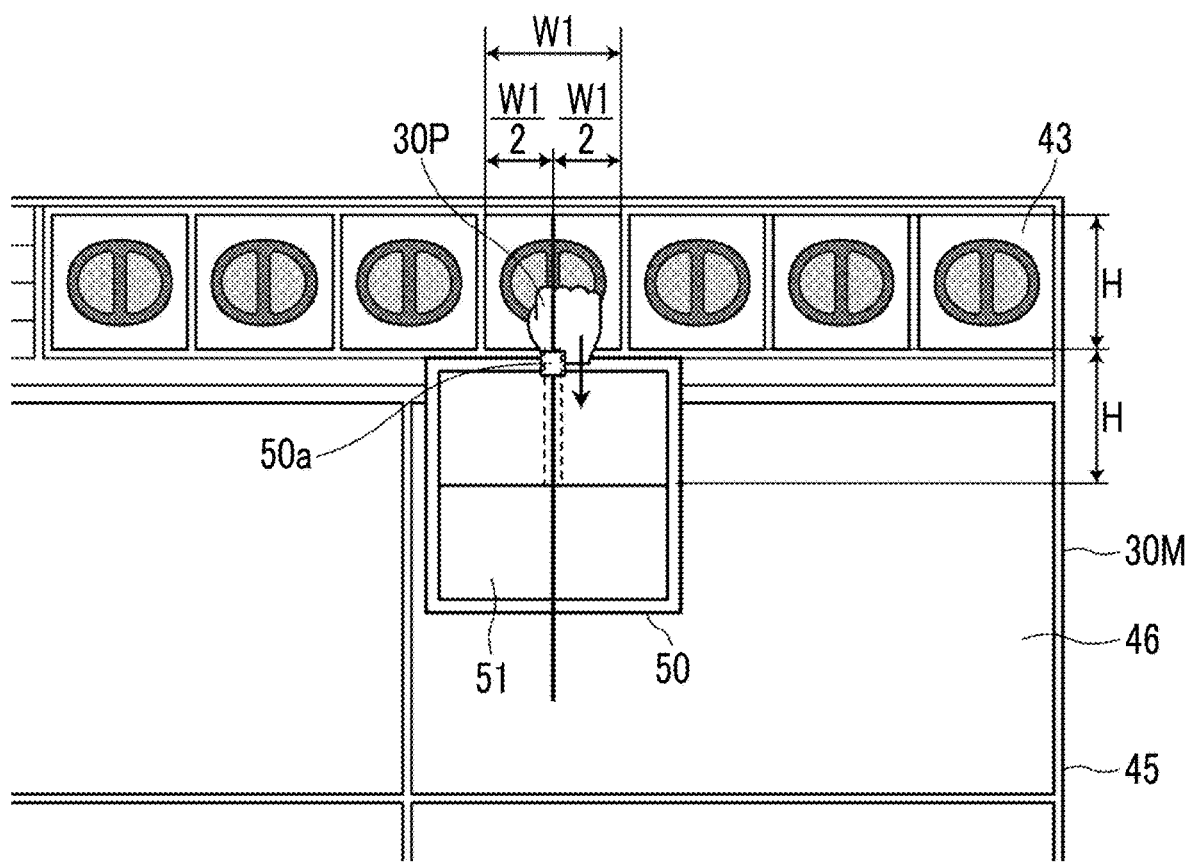
FIG. 24 is a diagram illustrating a display position of the miniature window.

According to the above-described embodiment, the miniature window 50 is disposed in the vicinity of the thumbnail image display region 43. Therefore, the user may drag the thumbnail image by a short distance as compared to a case in which the user performs the position designation operation using the image display region 45. Therefore, operability is improved. Here, the term "vicinity" means a position where the drag distance of the selected thumbnail image from the thumbnail image display region 43 to the designated position in the miniature window 50 is shorter than the drag distance of the selected thumbnail image from the thumbnail image display region 43 to the designated position in the image display region 45. Examples of a specific display position of the miniature window 50 include a position where a part of the miniature window 50 overlaps the thumbnail image display region 43 and a position where the lower side of the miniature window 50 overlaps the upper side of the image display region 45. Next, still another specific display position will be described. FIG. 24 is a diagram illustrating the display position of the miniature window 50.

As illustrated in FIG. 24, the miniature window 50 is displayed at a position where the upper side of the miniature window 50 overlaps the lower side of the thumbnail image display region 43 or is directly below the lower side of the thumbnail image display region 43. As illustrated in FIG. 24, the second display control unit 24 displays the miniature window 50 such that a midpoint 50a of the upper side of the miniature window 50 is located on a vertical line passing through the center of the width W1 of the dragged thumbnail image in the horizontal direction. That is, the center of the miniature window 50 and the center of the thumbnail image are aligned with each other in the horizontal direction.

In contrast, in the vertical direction, the second display control unit 24 displays the miniature window 50 such that the upper side of the miniature window 50 is located in the range of the same height H as the height H of the thumbnail image from the lower side of the dragged thumbnail image.

Figure 25:
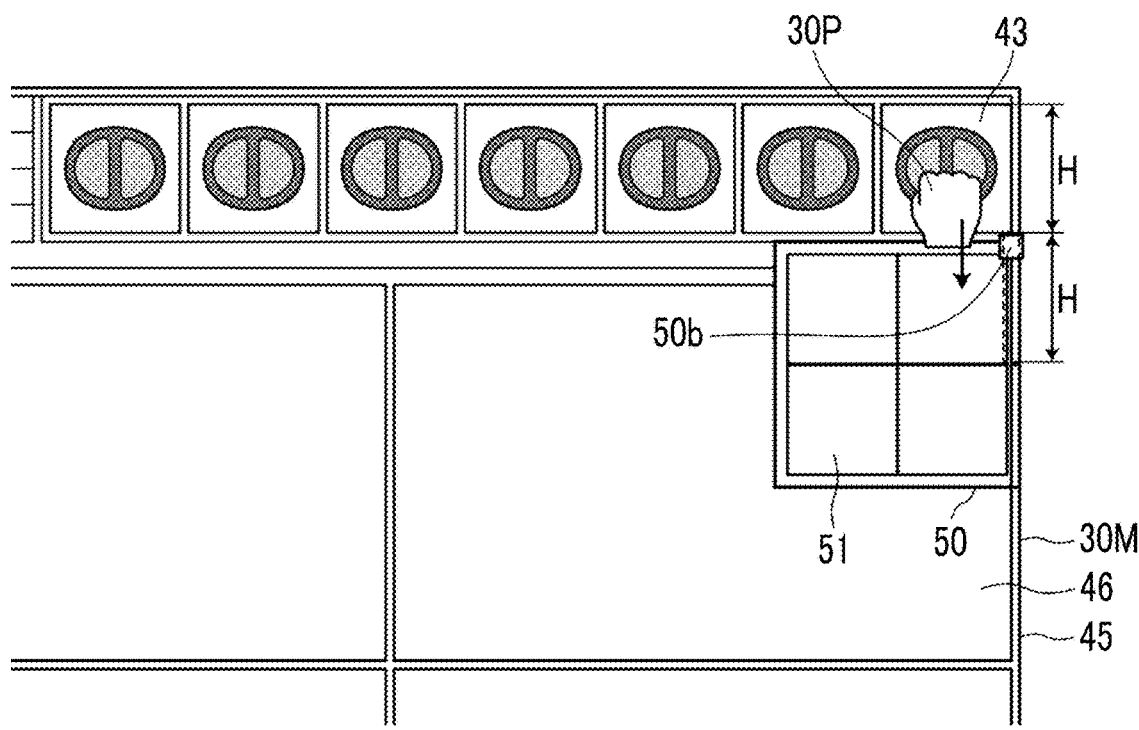
FIG. 25 is a diagram illustrating another display position of the miniature window.

Further, in a case in which the dragged thumbnail image is an image at the right end of the display screen 30M, the miniature window 50 may not fit within the display screen 30M and the center of the miniature window 50 and the center of the dragged thumbnail image may not be aligned with each other. In this case, the display position is different from that illustrated in FIG. 24. FIG. 25 is a diagram illustrating another display position of the miniature window 50.

As illustrated in FIG. 25, the miniature window 50 is displayed at a position where the upper side of the miniature window 50 overlaps the lower side of the thumbnail image display region 43 or is directly below the lower side of the thumbnail image display region 43. The second display control unit 24 displays the miniature window 50 such that a right end point 50b on the upper side of the miniature window 50 is located at the right end of the display screen 30M as illustrated in FIG. 25.

In contrast, in the vertical direction, the second display control unit 24 displays the miniature window 50 such that the upper side of the miniature window 50 is located in the range of the same height H as the height H of the thumbnail image from the lower side of the dragged thumbnail image as in FIG. 24.

Figure 26:
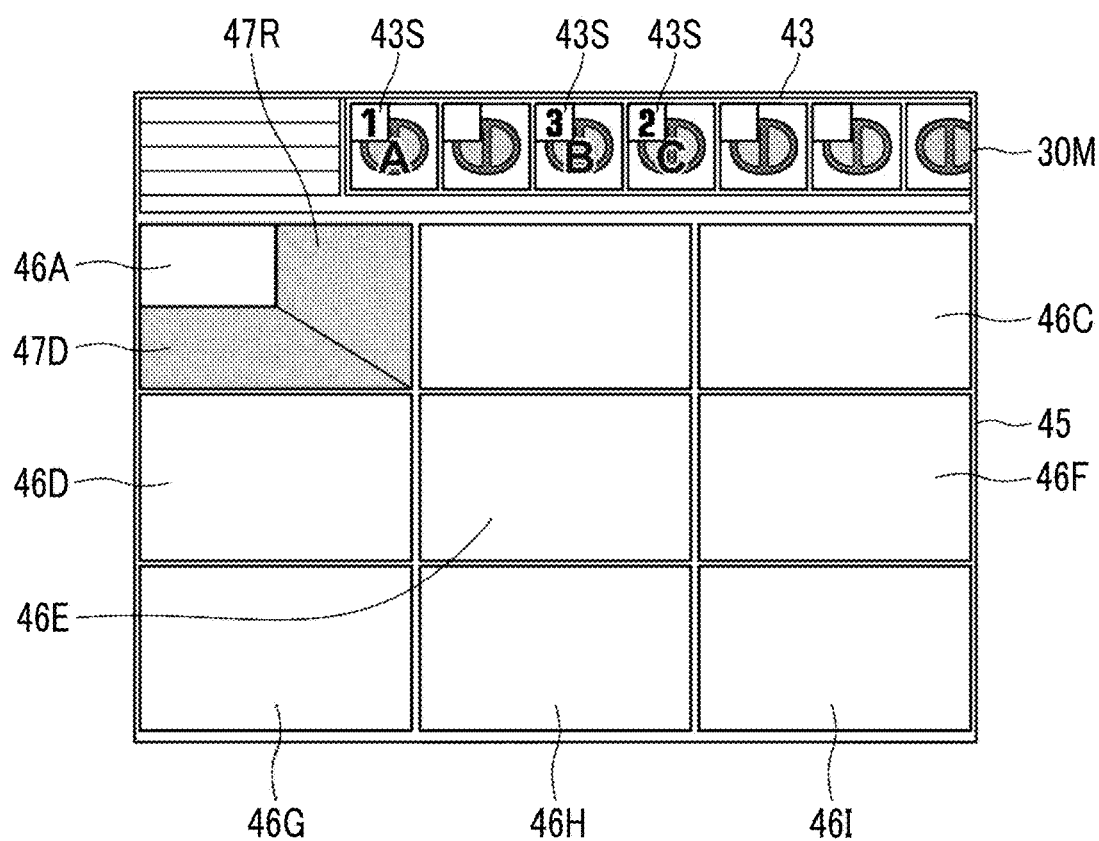
FIG. 26 is a diagram illustrating a position designation operation in a case in which the image display region is a designation window.

Next, Modification Example 2 of the first embodiment will be described. In the first embodiment, the designation window is the miniature window 50. However, in Modification Example 2, the image display region 45 in which a plurality of display frames 46 are arranged in a grid shape is used as the designation window. FIG. 26 is a diagram illustrating a position designation operation in a case in which the image display region 45 is used as the designation window.

In Modification Example 2, the miniature window 50 is not displayed and a horizontal direction designation region 47R and a vertical direction designation region 47D are set on each of nine display frames 46A to 46I which are arranged in the image display region 45. In Modification Example 2, the arrangement direction is designated by dragging a plurality of selected thumbnail images from the thumbnail image display region 43 to a designated position in the image display region 45 and dropping the thumbnail images at the designated position.

In Modification Example 2, since the miniature window 50 is not displayed, it is possible to prevent the image display region 45 from being hidden by the miniature window 50. This makes it easy to check the arrangement configuration of a plurality of display frames 46 in the image display region 45.

Modification Example 2 is the same as the first embodiment except that the designation window is the image display region 45. For example, the modification example of the first embodiment illustrated in FIGS. 18 to 23 can be applied to the horizontal direction designation region 47R and the vertical direction designation region 47D as in the case in which the miniature window 50 is used the designation window.

Next, a second embodiment of the present disclosure will be described. The mode of the operation of designating the arrangement direction in the first embodiment is the window mode. However, the mode of the operation of designating the arrangement direction in the second embodiment is a menu mode. The menu mode differs from the mode according to the first embodiment in the process of receiving the operation of designating the arrangement direction in Step ST4 in the flowchart illustrated in FIG. 7. Since the processes other than Step ST4 are the same as those in FIG. 7, the description thereof will not be repeated here.

Figure 27:
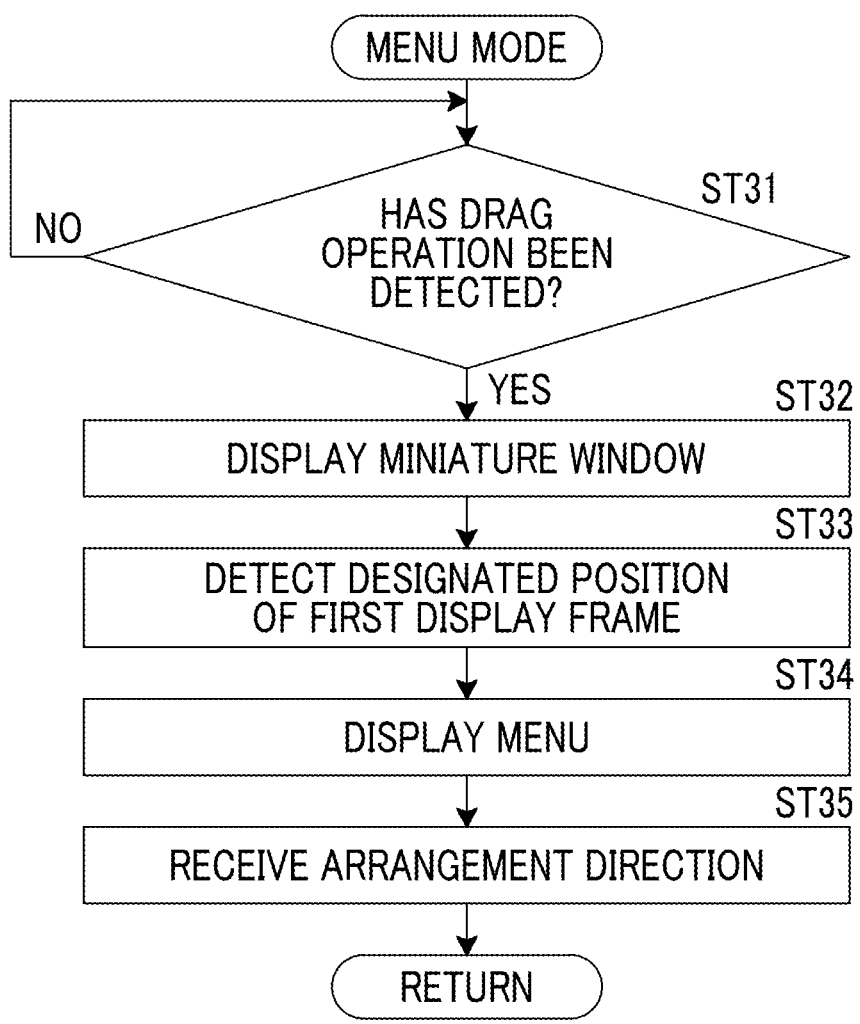
FIG. 27 is a flowchart illustrating a series of processes in a menu mode for receiving an arrangement direction designation operation.

FIG. 27 is a flowchart illustrating a series of processes in the menu mode which receives the operation of designating the arrangement direction. As illustrated in FIG. 27, first, the second receiving unit 23 detects whether or not a drag operation of dragging a plurality of thumbnail images selected in the thumbnail image display region 43 from the thumbnail image display region 43 has been performed (Step ST31). In a case in which the detection result in Step ST31 is "NO" (Step ST31; NO), the process in Step ST31 is repeated until the second receiving unit 23 detects a drag operation.

Figure 28:
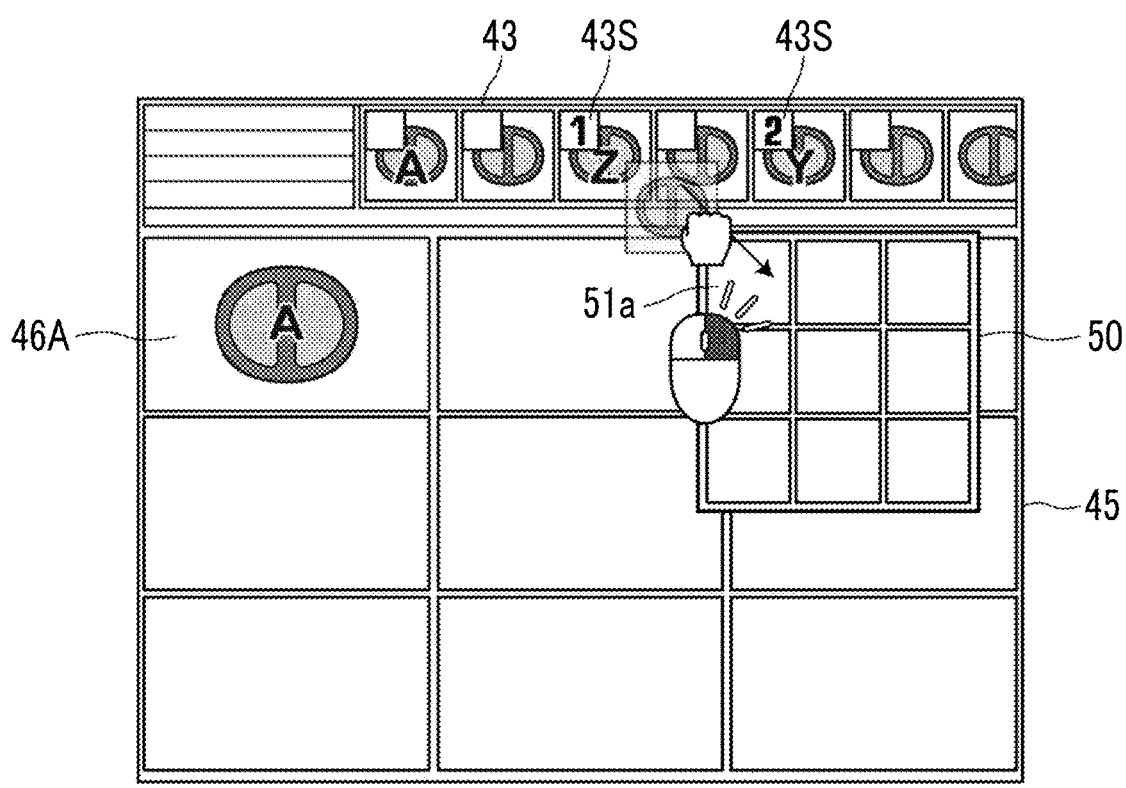
FIG. 28 is a diagram illustrating a position designation operation in the menu mode.

On the other hand, in a case in which the detection result in Step ST31 is "YES" (Step ST31; YES), the first display control unit 21 displays the miniature window 50 on the display screen 30M (Step ST32). FIG. 28 is a diagram illustrating a position designation operation in the menu mode.

As illustrated in FIG. 28, nine miniature display frames 51 which are arranged in a 3×3 grid shape are set in the miniature window 50 and the miniature window 50 is displayed in the display screen 30M separately from the image display region 45. In FIG. 28, since one examination image A has already been arranged in the display frame 46A of the image display region 45, the miniature display frame 51a corresponding to the position of the display frame 46A is displayed in a different aspect from other miniature display frames 51. For example, in the second embodiment, the miniature display frame 51*a* is displayed in a different color from the other miniature display frames 51. Further, as illustrated in FIG. 28, in the second embodiment, a thumbnail image Z is selected first and a thumbnail image Y is selected second.

Then, for example, the user drags a plurality of thumbnail images selected in the thumbnail image display region 43 to the miniature display frame 51*a* in the miniature window 50 while clicking the right button of the mouse. In a case in which the plurality of selected thumbnail images are dropped on the miniature display frames 51*a*, the second receiving unit 23 detects the miniature display frames 51*a* in the miniature window 50 as the designated position (Step ST33).

Figure 29:
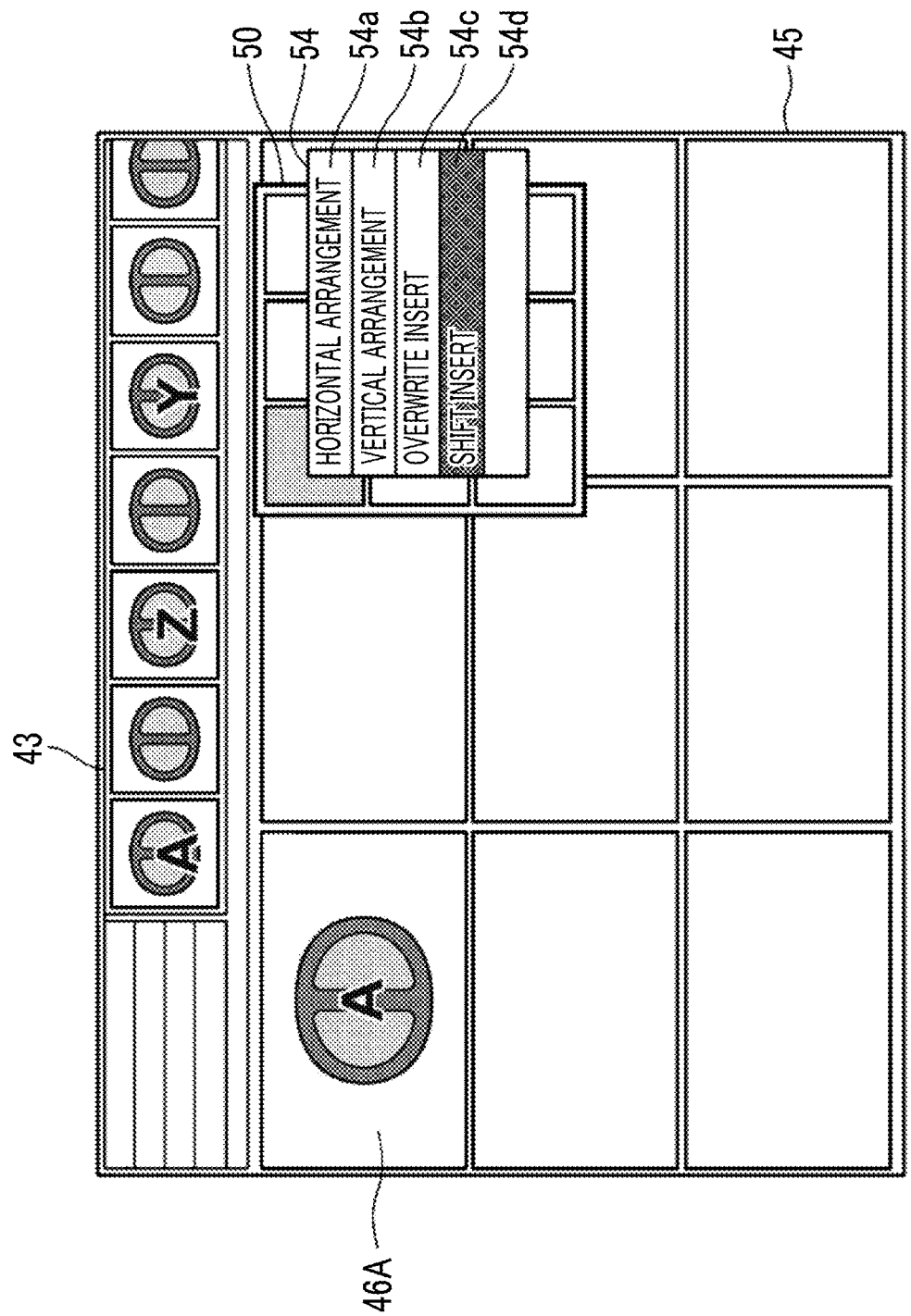
FIG. 29 is a diagram illustrating an example of menu display in the menu mode.

In a case in which the second receiving unit 23 detects the designated position (Step ST33), the second display control unit 24 displays a menu 54 (Step ST34). FIG. 29 is a diagram illustrating an example of menu display in the menu mode. The second display control unit 24 displays the menu 54 on the miniature window 50 as illustrated in FIG. 29. The menu 54 is configured such that the user can select any one of the items of horizontal arrangement 54*a*, vertical arrangement 54*b*, overwrite insert 54*c*, and shift insert 54*d*. For example, for the selection of an item in the menu 54, the user operates a scroll button of the mouse to highlight an item to be selected and clicks a left button of the mouse to select the highlighted item.

Here, the term "overwrite insert" means a method that, in a case in which there is an examination image that has already been laid out, replaces the examination image with an examination image to be newly laid out and inserts the examination image. In addition, the term "shift insert" means a method that, in a case in which there is an examination image that has already been laid out, shifts the display position of the laid-out examination image while inserting a new examination image to the position of the laid-out examination image.

The selection of an item is not limited to the above. The method of selecting an item may be appropriately changed. For example, the following configuration may be used: the user moves the pointer displayed on the display screen 30M to an item that the user wants to select using the mouse and then clicks the left button of the mouse to select the item.

In the second embodiment, as illustrated in FIG. 29, the shift insert 54*d* is selected. In a case in which the menu item is selected, the second receiving unit 23 receives the arrangement direction indicating "insertion while horizontally shifting" (Step ST35). The arrangement direction is a direction which has been set in advance as the arrangement direction. In this embodiment, the horizontal direction is set as the arrangement direction. As such, the reception of the operation of designating the arrangement direction by the menu mode is performed.

Figure 30:
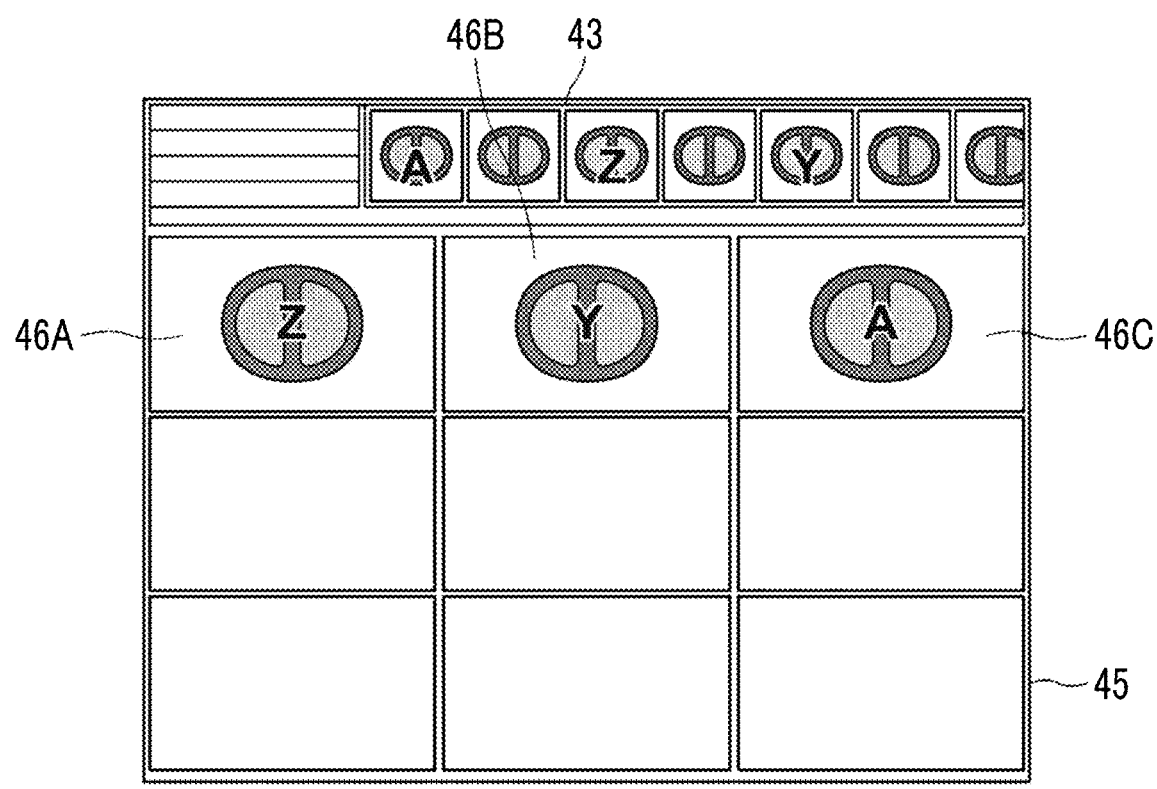
FIG. 30 is a diagram illustrating an example of a display screen on which a plurality of selected examination images are laid out.

In a case in which the menu mode is used, the second display control unit 24 lays out and displays an examination image Z and an examination image Y which correspond to the selected thumbnail image Z and the selected thumbnail image Y, respectively, in the display frames 46 of the image display region 45 in response to the designation of "insertion while horizontally shifting" received by the second receiving unit 23. FIG. 30 is a diagram illustrating an example of the display screen on which two selected examination images are laid out.

The second display control unit 24 shifts the examination image A which has already been disposed in the display frame 46A as illustrated in FIG. 29 by two grids corresponding to two selected examination images, that is, by two display frames in the right horizontal direction and displays the examination image A in the display frame 46C as illustrated in FIG. 30. Then, the second display control unit 24 sequentially lays out the examination image Z and the examination image Y in the horizontal direction, using the display frame 46A as the first display frame. Specifically, the second display control unit 24 lays out the examination image A in the display frame 46A and lays out the examination image Y in the display frame 46B. Then, the second display control unit 24 displays the examination images laid out in each display frame 46 on the display screen 30M.

According to the second embodiment, the menu mode is used to add "overwrite insert" and "shift insert" to the menu items. Therefore, for example, in a case in which an examination image has already been disposed in the display frame 46, it is possible to more easily achieve the arrangement of the examination images intended by the user.

Figure 31:
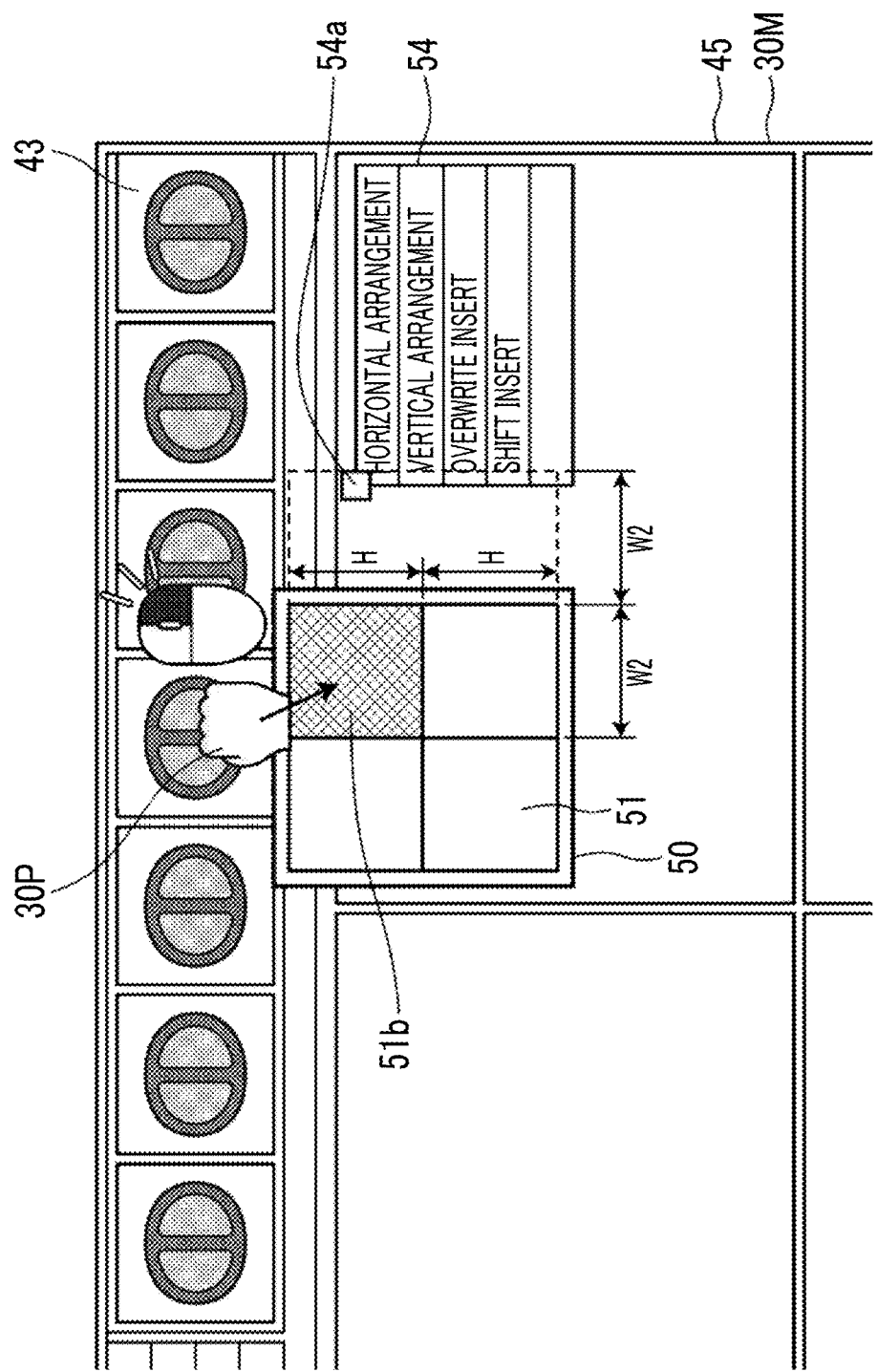
FIG. 31 is a diagram illustrating a display position of a menu.

In addition, since the display position of the miniature window 50 can be the same as that in the above-described embodiment, the description thereof will not be repeated. Hereinafter, the display position of the menu 54 will be described. In a case in which a plurality of selected thumbnail images are dragged while the right button of the mouse is being clicked and are then dropped on the miniature display frames 51, the second display control unit 24 displays the menu 54 on the basis of the miniature display frames 51 which are drop destinations. FIG. 31 is a diagram illustrating the display position of the menu 54. In FIG. 31, the miniature window 50 is displayed at a display position (see FIG. 24) where the center of the miniature window 50 and the center of the thumbnail image are aligned with each other. Further, in FIG. 31, four miniature display frames 51 are set in a 2×2 grid shape in the miniature window 50 and the drop destination is an upper right miniature display frame 51*b*.

As illustrated in FIG. 31, the second display control unit 24 displays the menu 54 such that an upper left vertex 54*a* of the menu 54 is located in a range that is twice (2×W2) the horizontal width W2 of the display frame 51*b* from the left side of the display frame 51*b*, which is the drop destination, to the right in the horizontal direction.

On the other hand, as illustrated in FIG. 31, the second display control unit 24 displays the menu 54 such that the upper left vertex 54*a* of the menu 54 is located in a range that is twice (2×H) the height H of the display frame 51*b* from the upper side of the display frame 51*b*, which is the drop destination, to the bottom in the vertical direction.

Figure 32:
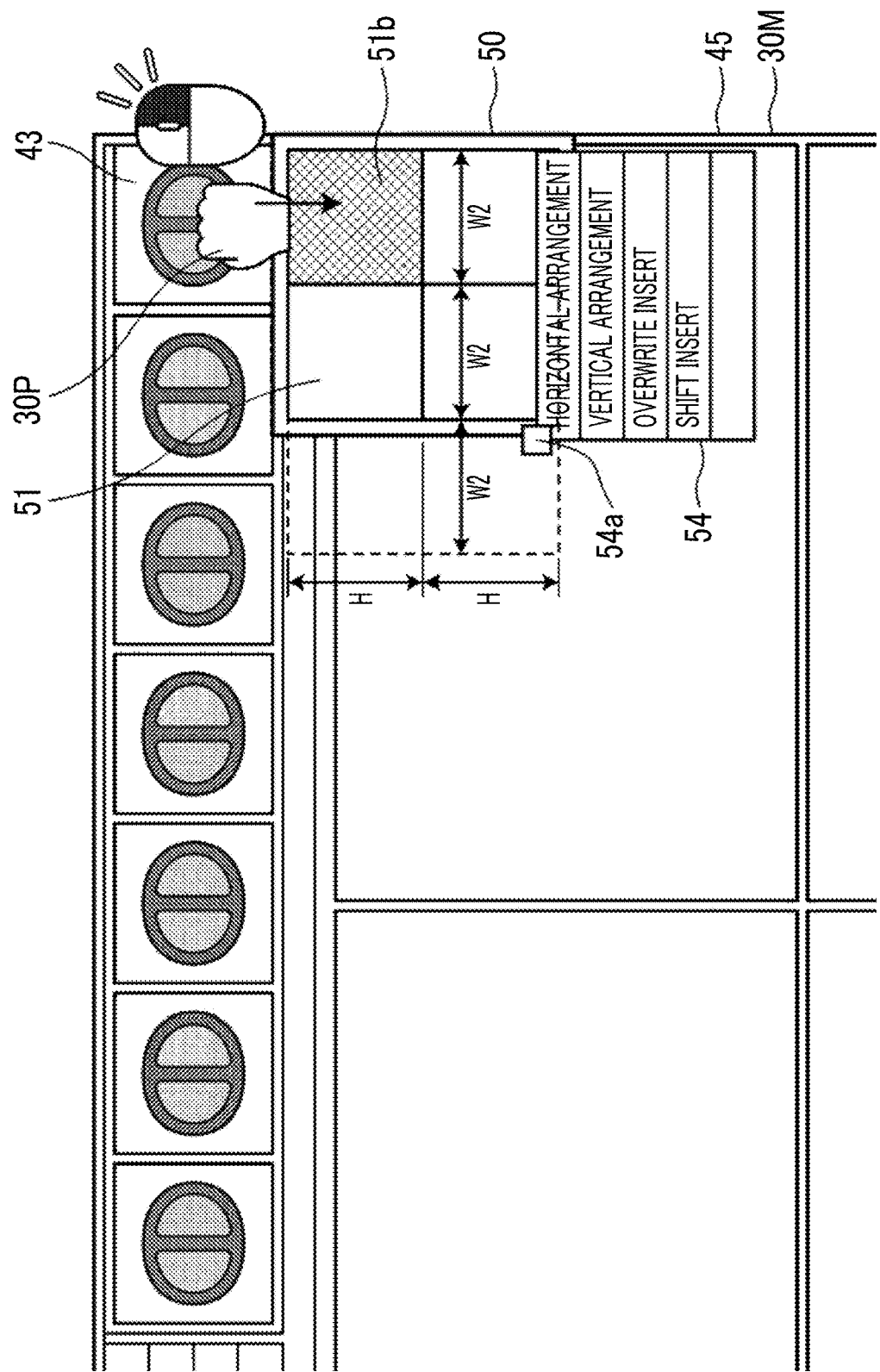
FIG. 32 is a diagram illustrating another display position of the menu.

Next, a case in which the miniature window 50 is located at a display position different from that in FIG. 24 will be described. FIG. 32 is a diagram illustrating another display position of the menu 54. In FIG. 32, the miniature window 50 is displayed at the display position (see FIG. 25) in a case in which the dragged thumbnail image is the rightmost image on the display screen 30M. In FIG. 32, four miniature display frames 51 are set in a 2×2 grid shape in the miniature window 50 and the drop destination is the upper right miniature display frame 51*b*.

As illustrated in FIG. 32, the second display control unit 24 displays the menu 54 such that the upper left vertex 54*a* of the menu 54 is located in a range that is three times (3×W2) the horizontal width W2 of the display frame 51*b* from the right side of the display frame 51*b*, which is the drop destination, to the left in the horizontal direction.

On the other hand, as illustrated in FIG. 31, the second display control unit 24 displays the menu 54 such that the upper left vertex 54a of the menu 54 is located in the range that is twice the height H of the display frame 51b from the upper side of the display frame 51b, which is the drop destination, to the bottom in the vertical direction.

Figure 33:
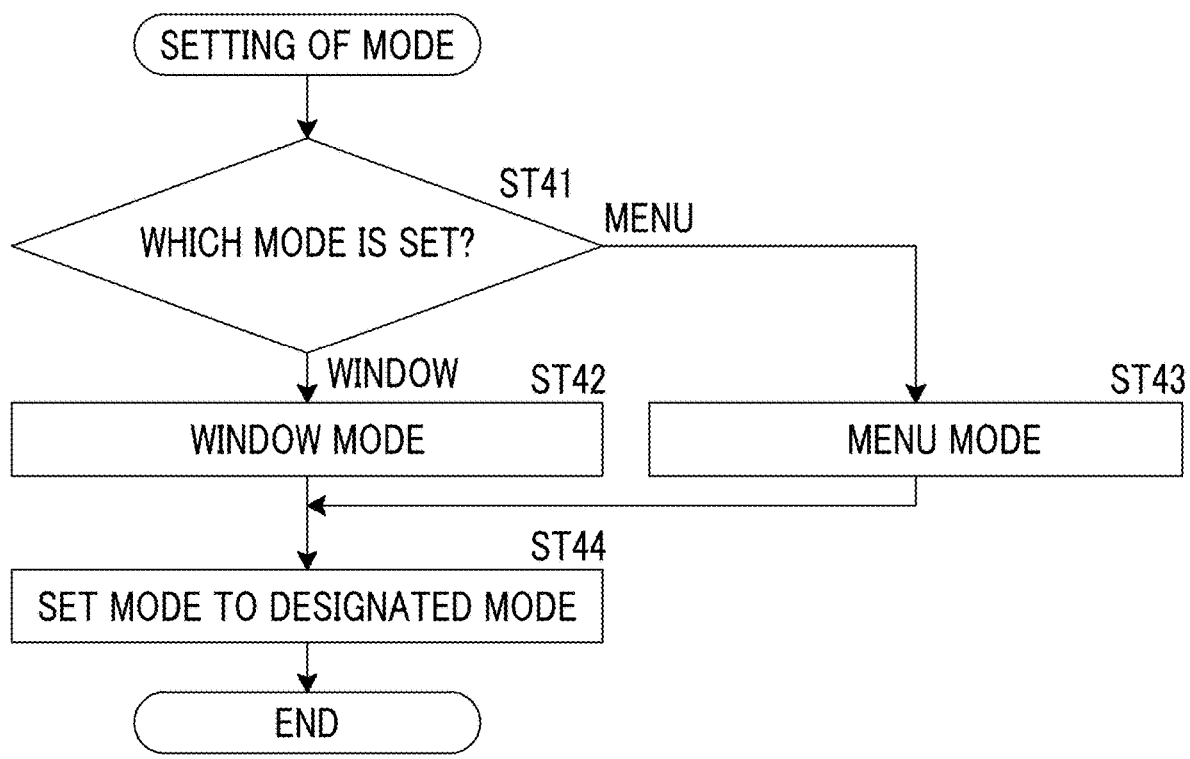
FIG. 33 is a flowchart illustrating a series of processes for setting a mode.

Next, a third embodiment of the present disclosure will be described. In the third embodiment, the mode can be selected between the window mode which is the mode of the operation of designating the arrangement direction in the first embodiment and the menu mode which is the mode of the operation of designating the arrangement direction in the second embodiment. This selection is performed, for example, by an operation of setting a setting screen mode. FIG. 33 is a flowchart illustrating a series of processes for mode setting.

In the third embodiment, for example, the second receiving unit 23 sets the mode of the operation of designating the arrangement direction. As illustrated in FIG. 33, the second receiving unit 23 determines the set mode (Step ST41). In a case in which the set mode is the window mode (Step ST41; grid), the second receiving unit 23 determines that the set mode is the window mode (Step ST42).

On the other hand, in a case in which the set mode is the menu mode in Step ST41 (Step ST41; menu), the second receiving unit 23 determines that the set mode is the menu mode (Step ST42).

Then, the second receiving unit 23 sets the mode of the operation of designating the arrangement direction as the designated mode (Step ST44) and ends a series of processes.

According to the third embodiment, it is possible to select the user's preferred designation operation mode and thus to improve user convenience.

In the above-described embodiments, one examination image is laid out in each display frame 46 of the image display region 45. However, the one examination image may be a representative image among same-series examination images acquired in the same examination. As described above, the same-series examination images are a plurality of slice images included in a series acquired by, for example, a CT examination. In a case in which the examination image displayed in the display frame 46 is a representative image, a representative image of same-series examination images in the display frame 46 can be selectively displayed, for example, by clicking the examination image currently displayed in the display frame 46.

Further, in the above-described embodiments, each of a plurality of slice images forming the three-dimensional image acquired by the three-dimensional imaging apparatus 2 is the examination image. However, the technology of the present disclosure is not limited thereto. For example, a two-dimensional image acquired by a two-dimensional imaging apparatus, such as a simple X-ray imaging apparatus, may be used as the examination image.

In the embodiment in which the miniature window 50 is displayed among the above-described embodiments, in a case in which an examination image has already been laid out in at least one display frame 46 in the image display region 45, related information related to the examination image that has been laid out may be displayed in the miniature display frame 51, that corresponds to the display frame 46 of the image display region 45 in which the examination image has been laid out, among a plurality of miniature display frames 51 in the miniature window 50.

Figure 34:
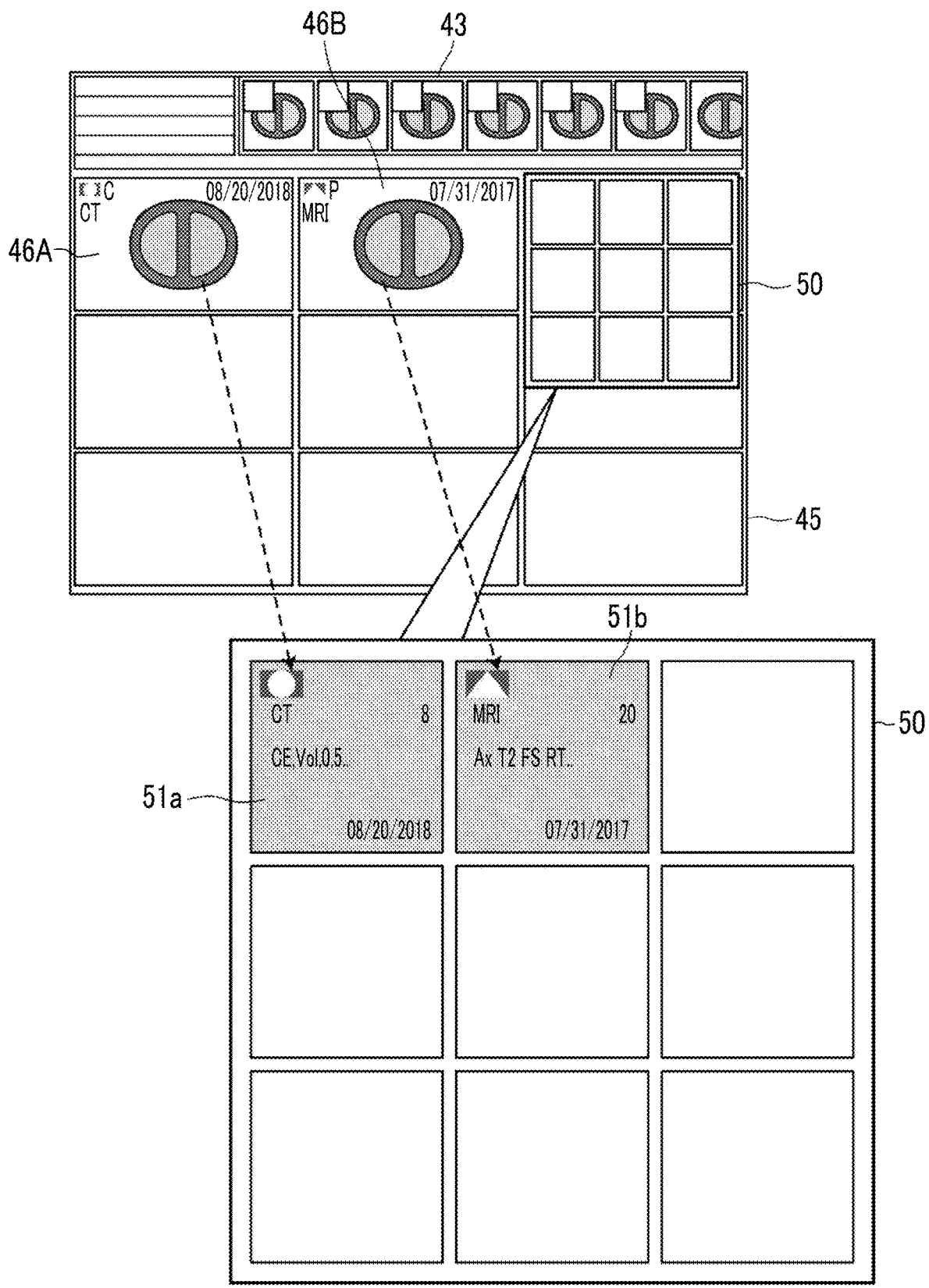
FIG. 34 is a diagram illustrating an example of the display of a miniature window in which information related to the examination image is displayed.

FIG. 34 is a diagram illustrating an example of the display of the miniature window 50 on which the related information of the examination image is displayed. As illustrated in FIG. 34, the first display control unit 21 displays, as the related information related to the examination images which have already been displayed in the display frames 46A and 46B, text information, such as the type of modality that has acquired the examination images, the date on which the examination images were acquired, and icons indicating the current examination and the past examination, in the miniature display frames 51a and 51b of the miniature window 50. Further, for example, in a case in which the examination image displayed in the display frame 46 is a representative image of same-series examination images (also referred to as a series) acquired in the same examination, text information indicating, for example, the number of same-series examination images and detailed information related to the series is displayed in the miniature display frames 51a and 51b of the miniature window 50.

Since the related information related to the examination image which has already been laid out in the display frame 46 is displayed in the miniature display frame 51, the user can see the miniature display frame 51 and check what kind of examination image is disposed in the display frame 46 in which the examination image has been laid out. Therefore, for example, the related information is referred to in a case in which the first display frame is designated in the miniature window 50 and convenience is improved.

In the related information related to the examination image, the text information includes at least one of a character, a number, or a symbol.

In the above-described embodiments, the viewer region 32 includes the patient information region 41, the examination list region 42, the thumbnail image display region 43, the toolbar region 44, and the image display region 45. However, the technology of the present disclosure is not limited thereto. The viewer region 32 may include at least the thumbnail image display region 43 and the image display region 45.

In the above-described embodiments, the first receiving unit 22 receives the selection order in which a plurality of thumbnail images are selected and the second display control unit 24 lays out a plurality of examination images in a plurality of display frames in the selection order. However, the technology of the present disclosure is not limited thereto. For example, for the examination images corresponding to each of the plurality of selected thumbnail images, it is possible to give an order to the examination images on the basis of the accessory information stored in the image storage server 3 together with the examination images. Specifically, in a case in which the examination images are included in same-series examination images in one same examination, the order may be given on the basis of the series number when same-series examination images are acquired.

For the arrangement order in the image display region 45, examples of the selection order of the thumbnail images include an order determined on the basis of any image attribute information in addition to the series number. Specific examples of the image attribute information include a collection date and time and a series description in addition to the series number. The collection date and time means the examination date and the examination time. For example, the arrangement order may be determined in chronological order of the examination date and in chronological order of the examination time or may be determined in reverse chronological order of the examination date and in reverse chronological order of the examination time. The series description means the type of three-dimensional imaging apparatus 2 (for example, a CT apparatus, an MRI apparatus, a PET apparatus, or a SPECT apparatus) used in one series, the imaging conditions (for example, whether or not a contrast agent is used or a radiation dose) during imaging in one series, and an examination part (imaging part) in one series. For example, the arrangement order may be determined from the head to the foot or may be determined from the foot to the head for each examination part. In addition, the order may be determined in a complex manner. First, the arrangement is performed by the series description, for example, a modality name and the arrangement is performed in the order of the collection date in the same modality.

For example, as illustrated in FIG. 8, even in a case in which the thumbnail image A, the thumbnail image C, and the thumbnail image B are selected in this order, the first receiving unit 22 may receive the order of the thumbnail image A, the thumbnail image B, and the thumbnail image C from the left end, regardless of the selection order. In this case, the reception order is not limited to the order from the left end and may be the order from the right end to the left. The direction in which the order is given can be set in advance by the user.

In addition, in FIGS. 11 to 16 of the above-described embodiments, the horizontal direction designation region 51R and the vertical direction designation region 51D are displayed in the same aspect (for example, in the same color). However, the present disclosure is not limited thereto. The horizontal direction designation region 51R and the vertical direction designation region 51D are displayed in different aspects (for example, in different colors). In the above-described embodiments, in each miniature display frame 51, the horizontal direction designation region 51R and the vertical direction designation region 51D are displayed in a different aspect (for example, in a different color) from regions other than the horizontal direction designation region 51R and the vertical direction designation region 51D. However, the technology of the present disclosure is not limited thereto. For example, the horizontal direction designation region 51R and the vertical direction designation region 51D may be displayed in the same aspect (for example, in the same color) as other regions. The reason is that, since the designated position may be detected, it is not necessary to allow the user to recognize the designation region.

Further, in the above-described embodiments, the second receiving unit 23 receives the operation of designating the vertical direction or the horizontal direction as the arrangement direction. However, the technology of the present disclosure is not limited thereto. For example, the second receiving unit 23 may receive the designation of an oblique direction.

In the above-described embodiments, the aspect in which only one display unit 30 is provided has been described. However, the technology of the present disclosure is not limited to the aspect in which one display unit (monitor) 30 is provided and may include a plurality of display units. In the case of a multi-monitor having a plurality of display units 30, for example, the display screen 30M is configured as follows.

A case in which a multi-monitor extended mode in which a plurality of monitors are virtually regarded as one monitor is used is considered. In this case, a monitor region in which one display screen can be displayed is extended. Therefore, in a case in which the display screen is enlarged and displayed, a portion that does not fit on a first monitor which is one monitor is displayed on a second monitor which is another monitor. For example, in a case in which there are eight (=2×4) display frames 46 in the display region of the display screen, four display frames 46 are displayed on the first monitor and the remaining four display frames 46 are displayed on the second monitor.

In this case, the second display control unit 24 can also treat the display screens or the display regions displayed on two monitors of the first monitor and the second monitor as one display screen or one display region. Further, the second display control unit 24 may treat the display screen or the display region displayed on the first monitor and the display screen or the display region displayed on the second monitor as independent display screens or display regions.

Figure 35:
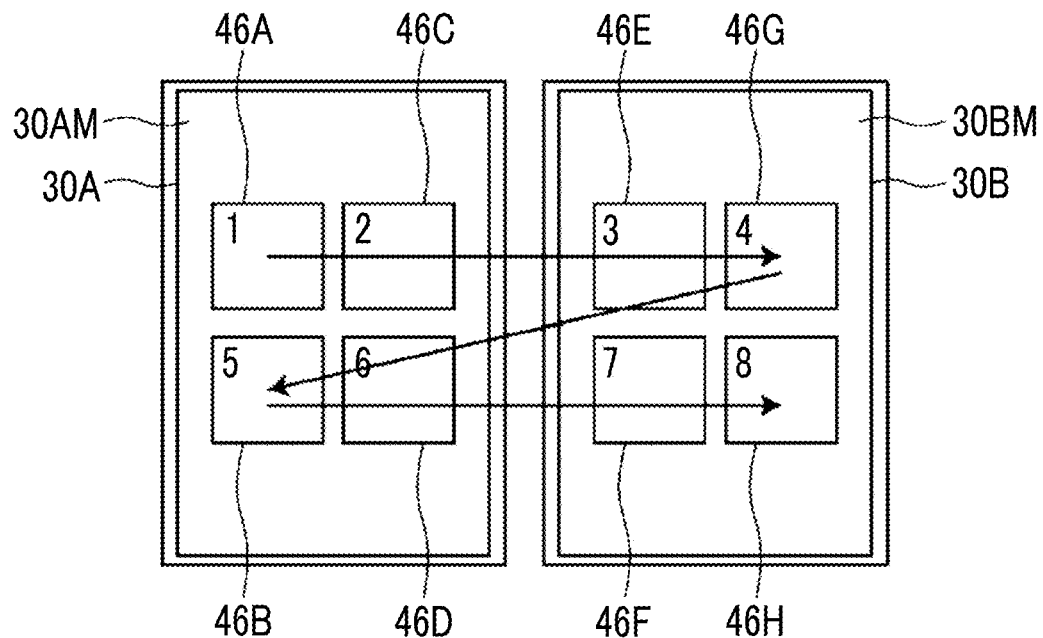
FIG. 35 is a diagram illustrating an example of display screens of two monitors.

In the former case, that is, the treatment of a plurality of display frames in the display region, in which the display screens or the display regions displayed on two monitors of the first monitor and the second monitor are treated as one display screen or one display region, is, for example, as illustrated in FIG. 35. FIG. 35 is a diagram illustrating an example of the display screens of two monitors.

In the example illustrated in FIG. 35, the second display control unit 24 treats a total of four display frames 46A to 46D and a total of four display frames 46E to 46H which are displayed in the upper or lower stages of a first monitor 30A and a second monitor 30B, respectively, as a series of display frames 46A to 46H. For example, in a case in which the arrangement direction received by the second receiving unit 23 is the horizontal direction, the order in which the eight display frames 46A to 46H are used is as follows: the display frames 46A, 46C, 46E, and 46G in the upper stage are prioritized; and, in a case in which the display frames 46A, 46C, 46E, and 46G in the upper stage are filled, the display is shifted to the display frames 46B, 46D, 46F, and 46H in the lower stage.

For example, numbers 1 to 4 are set to the display frames 46A, 46C, 46E, and 46G in the upper stage in order from the left display frame 46A of the first monitor 30A. Numbers 5 to 8 are set to the four display frames 46B, 46D, 46F, and 46H displayed in the lower stage in order from the left display frame 46B of the first monitor 30A. Therefore, in a case in which eight examination images are arranged in the eight display frames 46A to 46H, the examination images are arranged in order from the upper left side of the first monitor 30A to the upper right side of the second monitor 30B as represented by arrows in FIG. 35. In a case in which the four display frames 46A, 46C, 46E, and 46G in the upper stage are filled, the display is moved to the lower stage of the first monitor 30A and the examination images are arranged in order from the lower left side of the first monitor 30A to the lower right side of the second monitor 30B.

Figure 36:
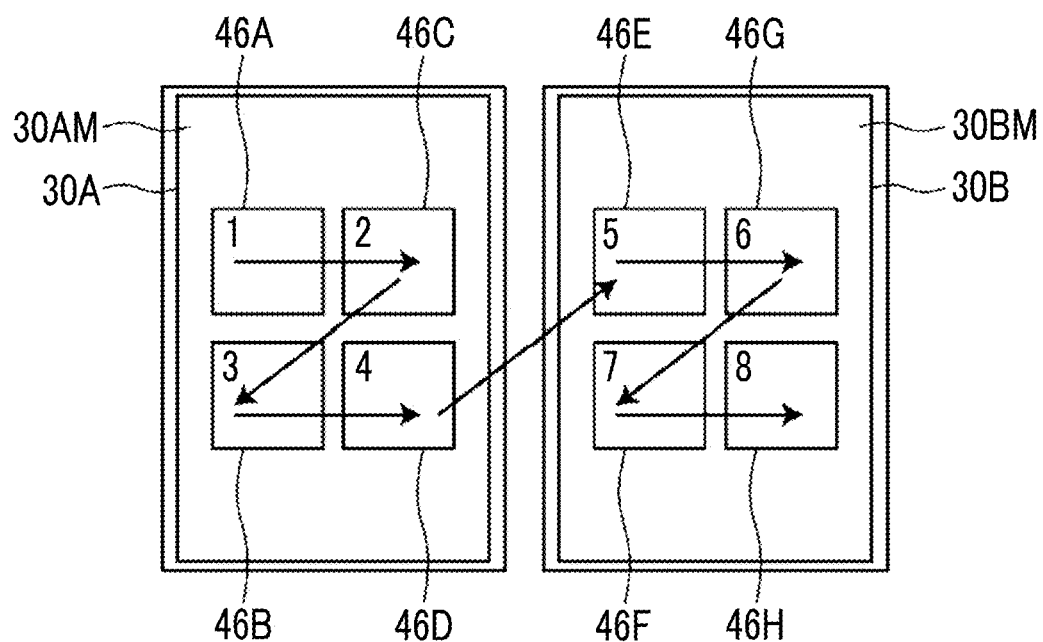
FIG. 36 is a diagram illustrating another example of the display screens of the two monitors.

In the latter case, that is, the treatment of a plurality of display frames in the display region, in which the display screen or the display region displayed on the first monitor and the display screen or the display region displayed on the second monitor are treated as independent display screens or display regions, is, for example, as illustrated in FIG. 36. FIG. 36 is a diagram illustrating an example of display screens of two monitors.

In the example illustrated in FIG. 36, unlike FIG. 35, the second display control unit 24 gives priority to four display frames 46A to 46D displayed on the first monitor 30A. In a case in which the four display frames 46A to 46D of the first monitor 30A are filled, the display is shifted to the second monitor 30B.

For example, numbers 1 to 4 are set to the display frames 46A to 46D of the first monitor 30A in order from the upper left display frame 46A to the lower right display frame 46D. Similarly, numbers 1 to 4 are set to the display frames 46E to 46H of the second monitor 30B in order from the upper left display frame 46E to the lower right display frame 46H.

Therefore, in a case in which eight examination images are arranged in the eight display frames 46A to 46H, the examination images are arranged in order from the upper left side of the first monitor 30A to the lower right side of the first monitor 30A as represented by arrows in FIG. 36. In a case in which the four display frames 46A to 46D of the first monitor 30A are filled, the display is moved to the upper left side of the second monitor 30B and the examination images are arranged in order from the upper left side of the second monitor 30B to the lower right side of the second monitor 30B.

The case in which the arrangement direction received by the second receiving unit 23 is the horizontal direction has been described. However, two monitors may also be used in a case in which the arrangement direction received by the second receiving unit 23 is the vertical direction. For example, in the aspect illustrated in FIG. 36, numbers may be set in the vertical direction in each of the first monitor 30A and the second monitor 30B.

Specifically, numbers 1 to 4 are set to the display frames 46A to 46D of the first monitor 30A such that number 1 is set to the upper left display frame 46A, number 2 is set to the lower left display frame 46B, number 3 is set to the upper right display frame 46C, and number 4 is set to the lower right display frame 46D, which is not illustrated. In a case in which the four display frames 46A to 46D of the first monitor 30A are filled, the display is moved to the upper left side of the second monitor 30B. Then, numbers 5 to 8 are set to the display frames 46E to 46H of the second monitor 30B such that number 5 is set to the upper left display frame 46E, number 6 is set to the lower left display frame 46F, number 7 is set to the upper right display frame 46G, and number 8 is set to the lower right display frame 46H. Therefore, in a case in which eight examination images are arranged in the eight display frames 46A to 46H, the examination images are arranged in order from the upper left side of the first monitor 30A to the lower right side of the first monitor 30A. Then, the examination images are arranged in order from the upper left side of the second monitor 30B to the lower right side of the second monitor 30B.

In addition, for example, in a case in which two monitors are arranged side by side in the vertical direction, numbers 1 to 4 are set to the left display frames 46A, 46B, 46E, and 46F in order from the left display frame 46A of the first monitor 30A, which is not illustrated. Numbers 5 to 8 are set to four display frames 46C, 46D, 46G, and 46H displayed on the right side in order from the right display frame 46C of the first monitor 30A. Therefore, in a case in which eight examination images are arranged in the eight display frames 46A to 46H, the examination images are arranged in order from the upper left side of the first monitor 30A to the lower left side of the second monitor 30B. In a case in which the left four display frames 46A, 46B, 46E, and 46F are filled, the display is moved to the right side of the first monitor 30A and the examination images are arranged in order from the upper right side of the first monitor 30A to the lower right side of the second monitor 30B.

In the above-described embodiments, for example, the following various processors can be used as the hardware structure of processing units performing various processes, such as the first display control unit 21, the first receiving unit 22, the second receiving unit 23, and the second display control unit 24. The various processors include, for example, a CPU which is a general-purpose processor executing software (program) to function as various processing units, a programmable logic device (PLD), such as a field programmable gate array (FPGA), which is a processor whose circuit configuration can be changed after manufacture, and a dedicated electric circuit, such as an application specific integrated circuit (ASIC), which is a processor having a dedicated circuit configuration designed to perform a specific process.

One processing unit may be configured by one of the various processors or a combination of two or more processors of the same type or different types (for example, a combination of a plurality of FPGAs or a combination of a CPU and an FPGA). In addition, a plurality of processing units may be configured by one processor.

A first example of the configuration in which a plurality of processing units are configured by one processor is an aspect in which one processor is configured by a combination of one or more CPUs and software and functions as a plurality of processing units. A representative example of this aspect is a client computer or a server computer. A second example of the configuration is an aspect in which a processor that implements the functions of the entire system including a plurality of processing units using one integrated circuit (IC) chip is used. A representative example of this aspect is a system-on-chip (SoC). As such, various processing units are configured by using one or more of the various processors as a hardware structure.

Furthermore, specifically, an electric circuit (circuitry) obtained by combining circuit elements, such as semiconductor elements, can be used as the hardware structure of the various processors.

What is claimed is:
1. A display control device comprising:
a processor, configured to
perform first display control to display, on a display screen, a display region in which a plurality of examination images acquired for each examination are displayed and which has a plurality of display frames arranged in a grid shape, each of the plurality of display frames being capable of having one of the plurality of examination images laid out therein, and a selection region which is used to select examination images to be laid out in the plurality of display frames from the plurality of examination images and in which a list of a plurality of thumbnail images is displayed, each of the plurality of thumbnail images being obtained by respectively reducing one of the plurality of examination images;
receive an operation of selecting thumbnail images from the plurality of thumbnail images displayed in the selection region to select the examination images corresponding to the selected thumbnail images;
receive a designation operation of designating an arrangement direction in which the selected examination images are arranged in the plurality of display frames in the display region in a state in which the selected thumbnail images are displayed in the selection region and before the selected examination images are laid out in the plurality of display frames and of designating a first display frame of the plurality of display frames; and
perform second display control to lay out the selected examination images from the first display frame in the plurality of display frames in the designated arrangement direction and to display the selected examination images laid out in the plurality of display frames on the display screen.

2. The display control device according to claim 1,
wherein the processor receives an operation of designating a vertical direction or a horizontal direction as the arrangement direction.

3. The display control device according to claim 2,
wherein a mode in which the processor receives the operation of designating the arrangement direction and the first display frame includes a window mode that uses either one of the display region in which the plurality of display frames are arranged or a miniature window which is displayed in the display screen separately from the display region and in which the arrangement of the plurality of display frames is reduced as a designation window for designating the arrangement direction and that receives the operation of designating the arrangement direction and the first display frame through the designation window.

4. The display control device according to claim 3,
wherein the designation operation is an operation of designating an inside or a frame line of one of the plurality of display frames in the designation window, and
wherein the processor receives a designation of the vertical direction or the horizontal direction as the arrangement direction according to a designated position in the inside or on the frame line.

5. The display control device according to claim 4,
wherein the processor sets the display frame including the designated position among the plurality of display frames as a first display frame of the selected examination images which are laid out.

6. The display control device according to claim 4,
wherein the operation of designating the arrangement direction through the designation window is an operation of dragging the plurality of thumbnail images selected in the selection region from the selection region to the designated position and dropping the thumbnail images at the designated position.

7. The display control device according to claim 6,
wherein the window mode uses the miniature window in which a plurality of miniature display frames are arranged as the plurality of display frames.

8. The display control device according to claim 7,
wherein, on the display screen, the miniature window is not displayed before the plurality of thumbnail images are selected and is displayed in a case in which the drag is started after the plurality of thumbnail images are selected.

9. The display control device according to claim 7,
wherein the miniature window is displayed at a position where a drag distance of the thumbnail image from the selection region to the designated position is shorter than in a case in which the display region is used as the designation window.

10. The display control device according to claim 3,
wherein the designation operation is an operation of designating an outer peripheral portion of the designation window, and
wherein the processor receives the designation of the vertical direction or the horizontal direction as the arrangement direction according to a designated position in the outer peripheral portion.

11. The display control device according to claim 3,
wherein the window mode uses the miniature window in which a plurality of miniature display frames are arranged as the plurality of display frames.

12. The display control device according to claim 11,
wherein, in a case in which an examination image has been laid out in at least one of the display frames in the display region,
related information related to the laid out examination image is displayed in a miniature display frame corresponding to a display frame of the display region in which the examination image has been laid out among the plurality of miniature display frames in the miniature window.

13. The display control device according to claim 12,
wherein the related information is text information.

14. The display control device according to claim 3,
wherein the mode in which the processor receives the operation of designating the arrangement direction includes a menu mode that displays a menu in which the vertical direction and the horizontal direction capable of being designated as the arrangement direction are displayed on the display screen and that receives the operation of designating the arrangement direction through the menu.

15. The display control device according to claim 14,
wherein either one of the window mode or the menu mode is selectable as the mode in which the processor receives the operation of designating the arrangement direction.

16. The display control device according to claim 3,
wherein the processor receives the operation of designating the arrangement direction by using the first display frame in the designation window.

17. The display control device according to claim 16,
wherein the designation operation is an operation of designating an inside or a frame line of the first display frame in the designation window, and
wherein the processor receives a designation of the vertical direction or the horizontal direction as the arrangement direction according to a designated position in the inside or on the frame line.

18. The display control device according to claim 2,
wherein the mode in which the processor receives the operation of designating the arrangement direction eludes a menu mode that displays a menu in which the vertical direction and the horizontal direction capable of being designated as the arrangement direction are displayed on the display screen and that receives the operation of designating the arrangement direction through the menu.

19. The display control device according to claim 1,
wherein the processor further receives a selection order in which the plurality of thumbnail images are selected, and
wherein the processor lays out the selected examination images in the plurality of display frames in the selection order.

20. The display control device according to claim 1,
wherein the examination images displayed in the display frames in the display region include a representative image of a plurality of examination images of each examination, and
wherein, in a case in which the examination image displayed in the display frame is the representative image, the plurality of examination images of each examination are capable of being selectively displayed in the display frame.

21. A method for operating a display control device, the method comprising:

a first display control step of performing first display control to display, on a display screen, a display region in which a plurality of examination images acquired for each examination are displayed and which has a plurality of display frames arranged in a grid shape, each of the plurality of display frames being capable of having one of the plurality of examination images laid out therein, and a selection region which is used to select examination images to be laid out in the plurality of display frames from the plurality of examination images and in which a list of a plurality of thumbnail images is displayed, each of the plurality of thumbnail images being obtained by respectively reducing one of the plurality of examination images;

a first receiving step of receiving an operation of selecting thumbnail images from the plurality of thumbnail images displayed in the selection region to select the examination images corresponding to the selected thumbnail images;

a second receiving step of receiving a designation operation of designating an arrangement direction in which the selected examination images are arranged in the plurality of display frames in the display region in a state in which the selected thumbnail images are displayed in the selection region and before the selected examination images are laid out in the plurality of display frames and of designating a first display frame of the plurality of display frames; and a second display control step of performing second display control to lay out the selected examination images from the first display frame in the plurality of display frames in the designated arrangement direction and to display the selected examination images laid out in the plurality of display frames on the display screen.

22. A non-transitory computer-readable storage medium storing therein a program for operating a display control device, the program causing a computer to function as:

a first display control unit that performs first display control to display, on a display screen, a display region in which a plurality of examination images acquired for each examination are displayed and which has a plurality of display frames arranged in a grid shape, each of the plurality of display frames being capable of having one of the plurality of examination images laid out therein, and a selection region which is used to select examination images to be laid out in the plurality of display frames from the plurality of examination images and in which a list of a plurality of thumbnail images is displayed, each of the plurality of thumbnail images being obtained by respectively reducing one of the plurality of examination images;

a first receiving unit that receives an operation of selecting thumbnail images from the plurality of thumbnail images displayed in the selection region to select the examination images corresponding to the selected thumbnail images;

a second receiving unit that receives a designation operation of designating an arrangement direction in which the selected examination images are arranged in the plurality of display frames in the display region in a state in which the selected thumbnail images are displayed in the selection region and before the selected examination images are laid out in the plurality of display frames and of designating a first display frame of the plurality of display frames; and a second display control unit that performs second display control to lay out the selected examination images from the first display frame in the plurality of display frames in the designated arrangement direction and to display the selected examination images laid out in the plurality of display frames on the display screen.

\* \* \* \* \*